(12) United States Patent
Gaynor et al.

(10) Patent No.: US 6,464,902 B1
(45) Date of Patent: *Oct. 15, 2002

(54) PERYLENE MIXTURES

(75) Inventors: Roger E. Gaynor, Oakville (CA);
James M. Duff, Mississauga (CA); C.
Geoffrey Allen, Waterdown (CA);
Gordon K. Hamer, Mississauga (CA);
Ah-Mee Hor, Mississauga (CA)

(73) Assignee: Xerox Corporation, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/579,255

(22) Filed: May 25, 2000

(51) Int. Cl.[7] .......... G03C 1/00; C07D 221/22; G03G 15/02

(52) U.S. Cl. .......... 252/600; 546/37; 430/59.1; 252/582

(58) Field of Search .............. 252/582, 600; 546/37; 430/59.1

(56) References Cited

U.S. PATENT DOCUMENTS

| | | | |
|---|---|---|---|
| 3,121,006 A | 2/1964 | Middleton et al. | 96/1 |
| 3,871,882 A | 3/1975 | Wiedemann | 96/1.5 |
| 3,904,407 A | 9/1975 | Regensburger et al. | 96/1.5 |
| 3,972,717 A | 8/1976 | Wiedemann | 96/1.5 |
| 3,992,205 A | 11/1976 | Wiedemann | 96/1.5 |
| 4,265,990 A | 5/1981 | Stolka et al. | 430/59 |
| 4,419,427 A | 12/1983 | Graser et al. | 430/59 |
| 4,429,029 A | 1/1984 | Hoffmann et al. | 430/57 |
| 4,469,769 A | 9/1984 | Nakazawa et al. | 430/78 |
| 4,514,482 A | 4/1985 | Loutfy et al. | 430/78 |
| 4,517,270 A | 5/1985 | Graser et al. | 430/58 |
| 4,555,463 A | 11/1985 | Hor et al. | 430/59 |
| 4,556,622 A | 12/1985 | Neumann et al. | 430/58 |
| 4,587,189 A | 5/1986 | Hor et al. | 430/59 |
| 4,709,029 A | 11/1987 | Spietschka et al. | 544/125 |
| 4,719,163 A | 1/1988 | Staudenmayer et al. | 430/58 |
| 4,746,741 A | 5/1988 | Staudenmayer et al. | 546/37 |
| 4,937,164 A | 6/1990 | Duff et al. | 430/58 |
| 4,968,571 A | 11/1990 | Gruenbaum et al. | 430/58 |
| 5,019,473 A | 5/1991 | Nguyen et al. | 430/58 |
| 5,225,307 A | 7/1993 | Hor et al. | 430/136 |
| 5,645,965 A | 7/1997 | Duff et al. | 430/59 |
| 5,683,842 A | 11/1997 | Duff et al. | 430/59 |
| 5,693,808 A | * 12/1997 | Langhals | 546/37 |
| 6,162,571 A | * 12/2000 | Duff et al. | 430/59.1 |
| 6,165,661 A | * 12/2000 | Hsiao et al. | 546/37 |
| 6,287,738 B1 | * 9/2001 | Duff et al. | 430/59.1 |

* cited by examiner

Primary Examiner—Philip Tucker
(74) Attorney, Agent, or Firm—E. O. Palazzo

(57) ABSTRACT

A process for the preparation of perylene mixtures comprised of at least two symmetrical perylene bisamide dimers of Formula 1

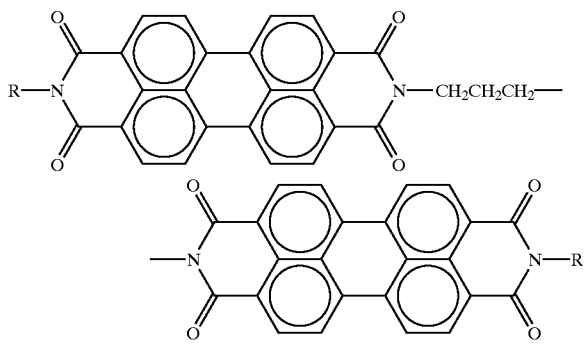

FORMULA 1 wherein R is hydrogen, alkyl, cycloalkyl, substituted alkyl, aryl, substituted aryl, aralkyl or substituted aralkyl, and at least one terminally unsymmetrical dimer of Formula 2

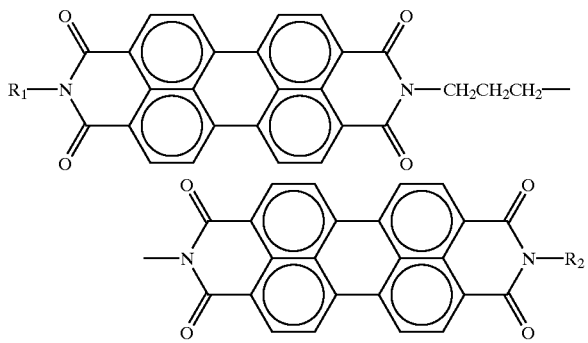

FORMULA 2 wherein $R_1$ and $R_2$ are hydrogen, alkyl, cycloalkyl, substituted alkyl, aryl, substituted aryl, aralkyl, or substituted aralkyl, and wherein $R^1$ and $R^2$ are dissimilar, which process comprises the condensation of a mixture of at least two perylene monoimide-monoanhydrides of Formula 3 with a diamine

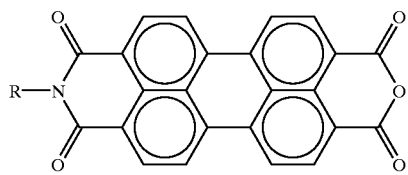

FORMULA 3 wherein R is hydrogen, alkyl, cycloalkyl, substituted alkyl, aryl, substituted aryl, aralkyl, and substituted aralkyl, with a 1,3-diaminopropane.

35 Claims, No Drawings

PERYLENE MIXTURES

COPENDING APPLICATION AND RELATED PATENTS

Illustrated in U.S. Pat. No. 6,162,571 are photoconductive imaging members containing unsymmetrical perylenes; in U.S. Pat. No. 5,645,965 there is illustrated photoconductive imaging members containing symmetrical dimeric perylenes, and in U.S. Pat. No. 5,683,842 there is illustrated photoconductive imaging members containing unsymmetrical dimer perylenes. The disclosures of each of the above copending application and U.S. patents are totally incorporated herein by reference.

Illustrated in U.S. Pat. No. 6,287,738, the disclosure of which is totally incorporated herein by reference, are photoconductive imaging members containing perylene composition mixtures.

The appropriate components of the above applications and patents, such as the substrate, perylenes, processes, charge transport and the like may be selected for the present invention in embodiments thereof.

BACKGROUND OF THE INVENTION

The present invention is directed generally to perylene mixtures of the following formulas, and photogenerating photoconductive members comprised of mixtures of environmentally acceptable, and substantially nontoxic, or nontoxic symmetrical perylene bisimide dimers of the Formula 1

FORMULA 1

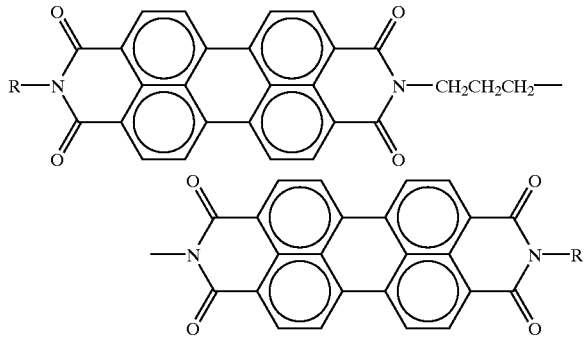

which dimers are illustrated in U.S. Pat. No. 5,645,965, the disclosure of which is totally incorporated herein by reference, and wherein R is, for example, hydrogen, alkyl, cycloalkyl, oxaalkyl, substituted alkyl, aryl, substituted aryl, aralkyl or substituted aralkyl, and the like, and Formula 2

FORMULA 2

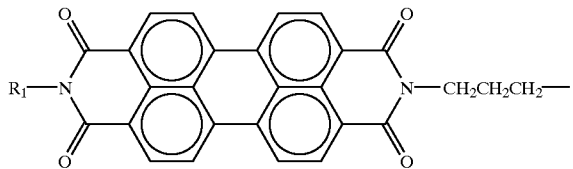

-continued

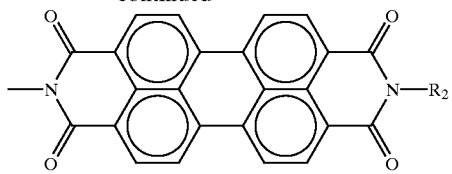

and wherein $R_1$ and $R_2$ is, for example, hydrogen, alkyl, cycloalkyl, substituted alkyl, aromatic, aryl, substituted aryl, aralkyl, substituted aralkyl, and the like, and wherein each of $R_1$ and $R_2$ is dissimilar, that is, each R represents a different group, for example one R can be alkyl, and $R_2$ can be aryl.

Alkyl includes linear and branched components with, for example, from 1 to about 25, and preferably from 1 to about 10 carbon atoms, such as methyl, ethyl, n-propyl, isopropyl, n-butyl, n-pentyl, 2-methylbutyl, heptyl, octyl, decyl, and the like. Cycloalkyl includes homologous rings from, for example, cyclopropane to cyclododecane. Substituted alkyl groups contain substituents such as hydroxy, alkoxy, carboxy, cyano, dialkylamino and the like. Aryl includes components with, for example, from 6 to about 24 carbon atoms such as phenyl, naphthyl, biphenyl, terphenyl and the like. Substituted aryl groups contain, for example, one to five substituents, such as alkyl like methyl, or tertiary-butyl, halogen (fluoro, chloro, bromo, and iodo), hydroxy, alkoxy like methoxy, nitro, cyano and dimethylamino. Aralkyl includes components with from 7 to about 24 carbon atoms such as benzyl, phenethyl, fluorenyl and the like. Substituted aralkyl groups can contain the same substituents as the aforementioned aryl groups, and more specifically, for example, methyl, tertiary-butyl, halogen, hydroxy, methoxy, nitro and dialkylamino.

The mixtures of perylene dimers illustrated herein can be selected as a photoactive component in photoconductive imaging members selected for electrophotographic printing, organic solar cells, chemical sensors, electroluminescent photoconductive members and other solid state optoelectronic photoconductive members utilizing photoconductors. Moreover, in embodiments the mixed dimers can be selected as a colorant in polymeric composite materials such as plastics, xerographic toners, and the like. Furthermore, the mixed perylene dimer pigments can be highly colored and can be prepared with a variety of hues such as orange, red, magenta, maroon, brown, black, greenish black, and the like, depending, for example, on the R substituents.

With the present invention in embodiments, photoconductive imaging members with the mixed perylene dimer pigments obtained by coupling two or more dissimilar perylene monoimides together, preferably via a propylene group, may enable a number of advantages with respect, for example, to photoconductive imaging members with monomeric perylene pigments or with pure symmetrical dimeric perylene pigments described in U.S. Pat. No. 5,645,965, the disclosure of which is totally incorporated herein by reference, internally unsymmetrical dimers described in U.S. Pat. No. 5,683,842, the disclosure of which is totally incorporated herein by reference, and pure terminally unsymmetrical dimers of the type described in copending application U.S. Ser. No. 09/165,595. For example, as illustrated in Table 2 below, photoconductive members comprising a photogenerator layer prepared from the pure dimer of Formula 1 wherein R is n-pentyl evidences a photosensitivity $E_{1/2}$ of 2.85 ergs/cm$^2$, the dimer corresponding to Formula 1 wherein R is 2-methylbutyl provided a sensitivity about 5.45 ergs/cm$^2$ and the pure, terminally unsymmetrical dimer corresponding to Formula 2 wherein $R_1$ is n-pentyl and $R_2$ is 2-methylbutyl indicated a sensitivity of 3.33 ergs/cm$^2$, whereas, as will be illustrated hereinafter, a similar photoconductive member prepared from a mixture of dimers prepared by the condensation of a 60:40 mixture of the monoimide corresponding to Formula 3 with R=n-pentyl and the monoimide corresponding to Formula 3 illustrated hereinafter with R=2-methylbutyl with 1,3-diaminopropane, which condensation results in the formation of an intimate mixture comprised of about 36 percent of the dimer corresponding to Formula 1 with R=n-pentyl, 16 percent of the dimer corresponding to Formula 1 wherein R=2-methylbutyl and about 48 percent of the dimer corresponding to Formula 2 wherein $R_1$=n-pentyl and $R_2$=2-methylbutyl, had a photosensitivity $E_{1/2}$=2.28 ergs/cm$^2$.

In embodiments, the present invention is directed to photogenerating pigments comprised of mixtures of symmetrical perylene bisimide dimers and terminally-unsymmetrical perylene bisimide dimers; and to an imaging member comprised of a supporting substrate, a photogenerating layer comprised of a mixture of symmetrical perylene dimers of Formula 1 and unsymmetrical dimers of Formula 2, and more specifically, wherein R, $R_1$ and $R_2$ are selected from hydrogen, methyl, ethyl, n-propyl, 3-hydroxypropyl, 3-methoxypropyl, n-butyl, isobutyl, sec-butyl, n-pentyl, 2-methylbutyl, 3-methylbutyl, neopentyl, n-hexyl, cyclohexyl, n-heptyl, n-octyl, phenyl, benzyl, 3-chlorobenzyl, phenethyl and the like, and a charge, especially hole, transport layer. Imaging members with the photogenerating pigments of the present invention are sensitive to wavelengths of, for example, from about 400 to about 700 nanometers, that is in the visible region of the light spectrum. Also, in embodiments thereof, the imaging members of the present invention generally possess broad spectral response to white light or, specifically to red, green and blue light emitting diodes and stable electrical properties over long cycling times. Many of the mixed perylene bisimide dimers of the present invention, when selected as photogenerator pigments, exhibit excellent charge acceptance of about a 800 volt surface potential in a layered photoconductive member, dark decay of, for example, less than about 100 volts per second, for example from about 40 to about 90, photosensitivities ranging from $E_{1/2}$ of less than about 3 to about 10 ergs, excellent dispersibility and low solubility in typical coating compositions, such as solutions of certain polymers in organic solvents, such as methylene chloride, toluene, cyclohexanone, tetrahydrofuran, chlorobenzene and butyl acetate, selected for the preparation of layered photoresponsive, or photoconductive imaging members. The mixed perylene dimers of the present invention can be selected as a substitute for selenium, such as trigonal selenium, in layered photoconductive imaging members, and further the imaging members of the present invention can be selected with red blue and green LED lasers for digital systems, and for upgraded visible light systems, and machines.

Also, the present invention in embodiments is directed to a process for the direct synthesis of mixtures of the Formula 1 and Formula 2 of dimers wherein the mixtures contain at least two different $R_1$ and $R_2$ groups, and where these groups may, for example, be approximately statistically distributed, such as, for example, between at least about 3 to about 35, for example, two different Rs provide 3, three Rs provide 6, 4, provide 10, five provide 15, and six groups provide 21. Further, embodiments of the present invention include a process for the preparation of substantially toxic free unsymmetrical perylene bisimide dimers in high yield and high purity, which process comprises the reaction of two or more perylene monoimido anhydrides of the following Formula 3 wherein R is, for example, as indicated herein with, for example, a suitable reactant, such as 1,3-diaminopropane in a high boiling solvent such as 1-methyl-2-pyrrolidinone, filtration and washing the resultant product with hot, for example about 50° C., solvents to remove residual starting components and other byproducts. For example, where equal amounts of two different monoimides, one having $R_1$ and the other $R_2$ as the nitrogen substituent, the mixture obtained after condensation with diaminopropane could be comprised of about 25 percent of the symmetric dimer represented by Formula 1, wherein both R groups are $R_1$, 25 percent of the corresponding dimer wherein both R groups are $R_2$ and about 50 percent of the unsymmetrical dimer represented by Formula 2, wherein $R_1$ and $R_2$ are dissimilar.

FORMULA 3

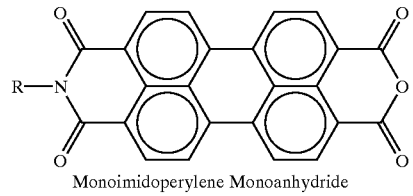

Monoimidoperylene Monoanhydride

Compounds of the type shown in Formula 3 have been described in the literature, see, for example, H. Troster, *Dyes and Pigments,* 4, 171–183, (1983), Y. Nagao et al, *Ibid,* 32, 71–83 (1996) and U.S. Pat. No. 4,709,029, the disclosures of which are totally incorporated herein by reference.

PRIOR ART

Generally, layered photoresponsive imaging members are described in a number of U.S. patents, such as U.S. Pat. No. 4,265,990, the disclosure of which is totally incorporated herein by reference, wherein there is illustrated an imaging member comprised of a photogenerating layer, and an aryl amine hole transport layer. Examples of photogenerating layer components include trigonal selenium, metal phthalocyanines, vanadyl phthalocyanines, and metal free phthalocyanines. Additionally, there is described in U.S. Pat. No. 3,121,006 a composite xerographic photoconductive member comprised of finely divided particles of a photoconductive inorganic compound dispersed in an electrically insulating organic resin binder. The binder materials disclosed in the '006 patent can comprise a material which is substantially incapable of transporting for any significant distance injected charge carriers generated by the photoconductive particles.

The selection of selected perylene pigments as photoconductive substances is also known. There is thus described in Hoechst European Patent Publication 0040402, DE3019326, filed May 21, 1980, the use of N,N'-disubstituted perylene-3,4,9,10-tetracarboxylic acid diimide pigments as photoconductive substances. Specifically, there is, for example, disclosed in this publication N,N'-bis(3-methoxypropyl) perylene-3,4,9,10-tetracarboxyldiimide dual layered negatively charged photoreceptors with improved spectral response in the wavelength region of 400 to 700 nanometers. A similar disclosure is presented in Ernst Gunther Schlosser, *Journal of Applied Photographic Engineering,* Vol. 4, No. 3, page 118 (1978). There are also disclosed in U.S. Pat. No. 3,871,882 photoconductive substances comprised of specific perylene-3,4,9,10-tetracarboxylic acid derivative dyestuffs. In accordance with the teachings of this patent, the photoconductive layer is preferably formed by vapor depositing the dyestuff in a vacuum. Also, there is specifically disclosed in this patent dual layer photoreceptors with perylene-3,4, 9,10-tetracarboxylic acid diimide derivatives, which have spectral response in the wavelength region of from 400 to 600 nanometers. Further, in U.S. Pat. No. 4,555,463, the disclosure of which is totally incorporated herein by reference, there is illustrated a layered imaging member with a chloroindium phthalocyanine photogenerating layer. In U.S. Pat. No. 4,587,189, the disclosure of which is totally incorporated herein by reference, there is illustrated a layered imaging member with a nonhalogenated perylene pigment photogenerating component. Both of the aforementioned patents disclose an aryl amine component as a hole transport layer.

Moreover, there are disclosed in U.S. Pat. No. 4,419,427 electrographic recording media with a photosemiconductive double layer comprised of a first layer containing charge carrier perylene diimide dyes, and a second layer with one or more compounds which are charge transporting materials when exposed to light, reference the disclosure in column 2, beginning at line 20. The two general types of monomeric perylene pigment, illustrated as follows in Formula 4, are commonly referred to as perylene bis(imides), 4a, and bis(imidazo) perylenes, 4b.

FORMULA 4

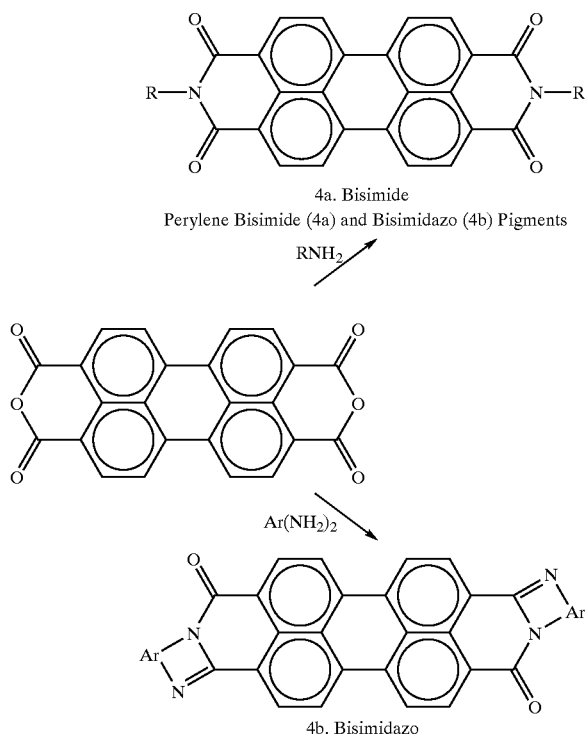

4a. Bisimide
Perylene Bisimide (4a) and Bisimidazo (4b) Pigments

4b. Bisimidazo wherein R is, for example, alkyl, aryl, aralkyl, and the like; Ar is, for example, 1,2-phenylene, 1,8-naphthalenediyl, and the like. These perylenes can, for example, be prepared by reacting perylene tetracarboxylic acid dianhydride with primary amines or with diamino-aryl or alkyl compounds. Their use as photoconductors is disclosed in U.S. Pat. No. 3,871,882, the disclosure of which is totally incorporated herein by reference, and U.S. Pat. No. 3,904,407. The '882 patent discloses the use of the perylene dianhydride and bisimides in general (Formula 4a, R=H, lower alkyl (C1 to C4), aryl, substituted aryl, aralkyl, a heterocyclic group or a NHR' group in which R' is phenyl, substituted phenyl or benzoyl) vacuum evaporated as thin charge generation layers (CGLs) in photoconductive members coated with a charge transporting layer (CTL). The '407 patent, the disclosure of which is totally incorporated herein by reference, illustrates the use of bisimide compounds (Formula 4a, R=alkyl, aryl, alkylaryl, alkoxyl or halogen, or heterocyclic substituent) with preferred pigments being R=chlorophenyl or methoxyphenyl. This patent illustrates the use of certain vacuum evaporated perylene pigments or a highly loaded dispersion of pigment in a binder resin as charge generating layer (CGL) in layered photoreceptors with a CTL overcoat or, alternatively, as a single layer photoconductive member in which the perylene pigment is dispersed in a charge transporting active polymer matrix. The use of purple to violet dyestuffs with specified chromaticity values, including bisimidazo perylenes, specifically cis and trans bis (benzimidazo)perylene (Formula 4b, X=1,2-phenylene) and bis(1,8-naphthimidazo)perylene (Formula 4b, X=1,8-naphthalenediyl), are disclosed in U.S. Pat. No. 3,972,717. The use of a plurality of pigments, inclusive of perylenes, in vacuum evaporated CGLs is illustrated in U.S. Pat. No. 3,992,205.

U.S. Pat. No. 4,419,427 discloses the use of highly-loaded dispersions of perylene bisimides, such as bis(2,6-dichlorophenylimide), in binder resins as CGL layers in photoconductive members overcoated with a charge transporting layer such as a poly(vinylcarbazole) composition. U.S. Pat. No. 4,429,029 illustrates the use, in photoconductive members similar to those of the '427 patent, of bisimides and bisimidazo perylenes in which the perylene nucleus is halogenated, preferably to an extent where 45 to 75 percent of the perylene ring hydrogens have been replaced by halogen. U.S. Pat. No. 4,587,189, the disclosure of which is totally incorporated herein by reference, illustrates layered photoresponsive imaging members prepared with highly-loaded dispersions or, preferably, vacuum evaporated thin coatings of cis- and trans-bis(benzimidazo)perylene (4a, X=1,2-phenylene) and other perylenes overcoated with hole transporting compositions comprised of a variety of N,N,N',N'-tetraaryl-4,4'-diaminobiphenyls. U.S. Pat. No. 4,937, 164 illustrates the use of perylene bisimides and bisimidazo pigments in which the 1,12- and/or 6,7 position of the perylene nucleus is bridged by one or two sulfur atoms wherein the pigments in the CGL layers are either vacuum evaporated or dispersed in binder resins and a layer of tetraaryl biphenyl hole transporting molecules.

U.S. Pat. No. 4,517,270 illustrates bisimides with propyl, hydroxypropyl, methoxypropyl and phenethyl substituents (4a, R=$CH_3CH_2CH_2$—, $HOCH_2CH_2CH_2$—, $CH_3OCH_2CH_2CH_2$—, and $C_6H_5CH_2CH_2$—) which are black or dark primarily because of their crystal properties, and perylene pigments which are nuclearly substituted with anilino, phenylthio, or p-phenylazoanilino groups. Pigments of this type were indicated as providing good electrophotographic recording media with panchromatic absorption characteristics. Similarly, in U.S. Pat. Nos. 4,719,163 and 4,746, 741 the 4a, R=3-methyl-$C_6H_5CH_2CH_2$—) is indicated as providing layered electrophotographic photoconductive members having spectral response to beyond 675 nanometers.

Other patents relating to the use of perylene pigments in layered photoreceptors are U.S. Pat. No. 5,019,473, which illustrates a grinding process to provide finely and uniformly dispersed perylene pigment in a polymeric binder with excellent photographic speed, and U.S. Pat. No. 5,225,307, the disclosure of which is totally incorporated herein by reference, which discloses a vacuum sublimation process which provides a photoreceptor pigment, such as bis (benzimidazo)perylene (4b, X=1,2-phenylene) with superior electrophotographic performance.

The following patents relate to the use of perylene compounds, for example, either as dissolved dyes or as dispersions in single layer electrophotographic photoreceptors usually based on sensitized poly(vinyl carbazole) compositions: U.S. Pat. Nos. 4,469,769; 4,514,482 and 4,556,622.

Dimeric perylene bisimide pigments are also known, reference for example U.S. Pat. No. 4,968,571. Dimeric, trimeric and tetrameric perylene bisimide pigments wherein the perylene imide nitrogens are attached to a carbocyclic or heterocyclic radical have been described in European Patent EP 0 711 812 A1.

Also, U.S. Pat. No. 5,645,965, the disclosure of which is totally incorporated herein by reference, illustrates symmetrical perylene bisimide dimers of the type illustrated in Formula 1, wherein the 1,3-propylene bridge is replaced by a variety of alkyl, aryl or aralkyl groups, and U.S. Pat. No. 5,683,842, the disclosure of which is totally incorporated herein by reference, describes internally unsymmetrical bisimide dimers.

While the above described layered perylene-based photoreceptors, or photoconductive imaging members may exhibit desirable xerographic electrical characteristics, the mixed perylene bisimide dimers of the present invention, can exhibit, on the average, higher photosensitivities as indicated by the measured $E_{1/2}$ values. This measurement, which is used routinely in photoreceptor technology, refers, for example, to the energy required (in ergs/square centimeter) to discharge a photoreceptor from an initial surface charge to one half of this initial value, for example, from 800 to 400 volts surface potential. For example, an $E_{1/2}$ value of about 10 to about 12 Erg/cm$^2$ could be considered acceptable, about 5 to about 10 Erg/cm$^2$ good, and values equal to or below about 5 Erg/cm$^2$, such as about 1 to about 5 as excellent. As shown in Table 1, hereinafter, the invention photoreceptors prepared, for example, by using dissimilar mixed symmetrical and unsymmetrical dimers provided excellent sensitivities with $E_{1/2}$ values ranging, for example, from 2.28 to 3.13 ergs/cm$^2$.

Additionally, although a number of known imaging members are suitable for their intended purposes, a need remains for imaging members containing substantially non-toxic photogenerator pigments. In addition, a need exists for imaging members containing photoconductive components with excellent xerographic electrical performance including higher charge acceptance, lower dark decay, increased charge generation efficiency and charge injection into the transporting layer, tailored PIDC curve shapes to enable a variety of reprographic applications, reduced residual charge and/or reduced erase energy, improved long term cycling performance, and less variability in performance with environmental changes in temperature and relative humidity in combination with excellent $E_{1/2}$ characteristics. There is also a need for imaging members with photoconductive components comprised of certain photogenerating pigments with enhanced dispersibility in polymers and solvents. There is also a need for photogenerating pigments which permit the preparation of coating dispersions, particularly in dip-coating operations, which are colloidally stable and wherein settlement is avoided or minimized, for example little settling for a period of from 20 to 30 days in the absence of stirring. Further, there is a need for photoconductive materials with enhanced dispersibility in polymers and solvents that enable low cost coating processes in the manufacture of photoconductive imaging members. Additionally, there is a need for photoconductive materials that enable imaging members with enhanced photosensitivity in the red region of the light spectrum, enabling the resulting imaging members thereof to be selected for imaging by red diode and gas lasers. Furthermore, there is a need for photogenerator pigments with spectral response in the green and blue regions of the spectrum to enable imaging by newly emerging blue and green electronic imaging light sources. A need also exists for improved panchromatic pigments with broad spectral response from about 400 to 700 nanometers for color copying using light-lens processes. There also is a need for photogenerating pigments that can be readily prepared from commercially available reactants, and for preparative processes and purification techniques which provide highly pure pigment with outstanding xerographic electrical performance, without recourse to time consuming post-synthetic purification methods such as solvent extraction or vacuum sublimation that can add one to about 5 days to the preparative procedure for a given pigment. These and other needs may be accomplished, it is believed, in embodiments of the present invention, and more specifically, these needs may be accomplished in combination with excellent $E_{1/2}$ characteristics.

SUMMARY OF THE INVENTION

Examples of features of the present invention include:

It is a feature of the present invention to provide improved environmentally acceptable mixtures of symmetrical and unsymmetrical perylene bisimide dimers and imaging members thereof with many of the advantages illustrated herein.

It is another feature of the present invention to provide imaging members with novel photoconductive perylene mixture components with improved photoconductivity.

Additionally, in another feature of the present invention there are provided (1) mixed perylene bisimide dimers suitable for use as dispersed colorants in polymeric composites and as photogenerator pigments in layered photoconductive imaging photoconductive members; (2) mixed perylene bisimide dimers comprised of two or more dissimilar perylene bisimide moieties joined together by a 1,3-propylene group; processes for the preparation of dimeric mixed pigments from readily available starting materials; and (3) processes for the purification of mixed dimers which enable photoelectrically stable materials for their selection as photogenerator pigments in photoconductive imaging photoconductive members, or members.

It is another feature of the present invention to provide photoconductive imaging members with mixtures of symmetrical and unsymmetrical perylene dimer photogenerating pigments with the formulas illustrated herein, and that enable imaging members with improved photosensitivity in the visible wavelength region of the light spectrum, such as from about 400 to about 700 nanometers.

It is another feature of the present invention to provide mixed dimeric pigments which can possess a variety of colors, such as magenta, red, brown, black, green, and the like; the color being primarily dependent on the types of terminal groups selected.

Still another feature of the present invention relates to the provision of novel mixed compounds, and more specifically, compounds of the formulas illustrated herein.

Another feature of the present invention relates to photoconductive imaging members wherein there is added to the photogenerator layer, especially a layer containing a binder like polyvinyl-butyral (PVB) a component, such as polyvinyl-carbazole (PVK), thereby for example, allowing increases in photosensitivity without adversely effecting the electrical stability of the member, or by adding an electron transport molecule, such as 4-n-butoxy carbonyl-9-fluorenyl malonitrile (BCFM), TNF (trinitro-9-fluorene), vinylcarbazole, and the like, including polymers thereof and which components are added in effective suitable amounts, such as from about 0.5 to about 10, and more specifically, from about 1 to about 5 weight percent.

Aspects of the present invention relate to a process for the preparation of perylene mixtures comprised of at least two symmetrical perylene bisamide dimers of Formula 1

FORMULA 1

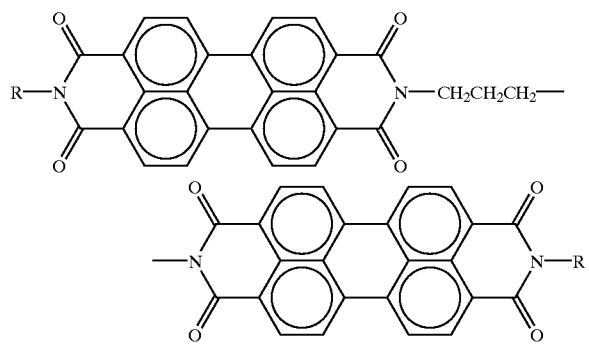

wherein R is hydrogen, alkyl, cycloalkyl, substituted alkyl, aryl, substituted aryl, aralkyl or substituted aralkyl, and at least one terminally unsymmetrical dimer of Formula 2

FORMULA 2

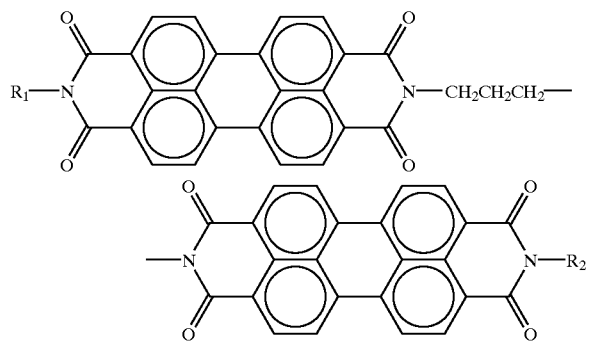

wherein $R_1$ and $R_2$ are hydrogen, alkyl, cycloalkyl, substituted alkyl, aryl, substituted aryl, aralkyl, or substituted aralkyl, and wherein $R_1$ and $R_2$ are dissimilar, which process comprises the condensation of a mixture of at least two perylene monoimide-monoanhydrides of Formula 3 with, for example, a diamine

FORMULA 3

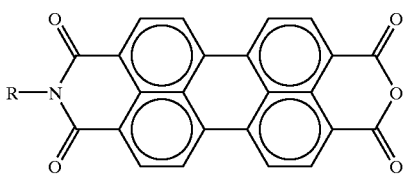

wherein R is hydrogen, alkyl, cycloalkyl, substituted alkyl, aryl, substituted aryl, aralkyl, and substituted aralkyl, with a 1,3-diaminopropane; a composition comprised of a mixture of at least two symmetrical perylene bisimide dimers of Formula 1

FORMULA 1

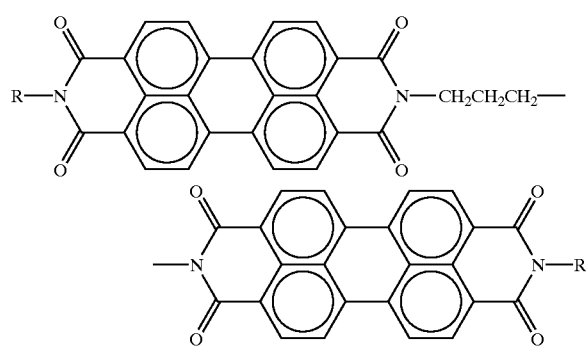

wherein R is hydrogen, alkyl, cycloalkyl, substituted alkyl, aryl, substituted aryl, aralkyl or substituted aralkyl, and at least one terminally unsymmetrical dimer of Formula 2

FORMULA 2

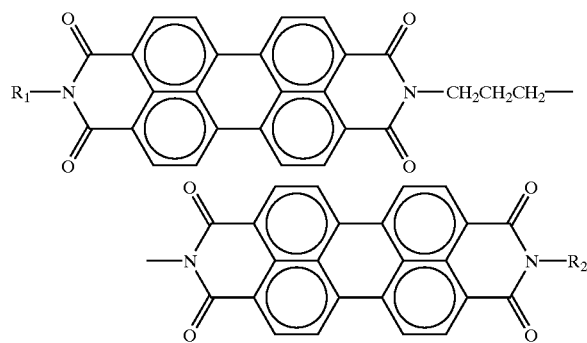

wherein $R_1$ and $R_2$ are hydrogen, alkyl, cycloalkyl, substituted alkyl, aryl, substituted aryl, aralkyl, or substituted aralkyl, and wherein $R_1$ and $R_2$ are dissimilar; layered imaging members comprised of a supporting substrate, a photogenerating layer thereover comprised of photogenerating pigments comprised of a mixture of from about 3 to about 12 symmetrical and unsymmetrical perylene bisimide dimers, such as those of Formula 1 and Formula 2, and more specifically, wherein each $R_1$ and $R_2$ is dissimilar and is for example, hydrogen, alkyl, such as methyl, ethyl, n-propyl, n-butyl, isobutyl, n-pentyl, 2-methylbutyl, 3-methylbutyl, n-hexyl, phenyl, benzyl, phenethyl and the like; imaging members comprised of, preferably in the order indicated, a conductive substrate, a photogenerating layer comprising the mixed perylene bisimide dimer pigments illustrated herein dispersed in a resinous binder composition, and a charge transport layer, which comprises charge transporting molecules dispersed in an inactive resinous binder composition; a photoconductive imaging member comprised of a conductive substrate, a hole transport layer comprising a hole transport composition, such as an aryl amine, dispersed in an inactive resinous binder composition, and as a top layer a photogenerating layer comprised of mixed perylene bisimide dimer pigments optionally dispersed in a resinous binder composition; and an imaging member comprised of a conductive substrate, a hole blocking metal oxide layer, an optional adhesive layer, a photogenerating layer comprised of the mixed perylene bisimide dimer pigments of the present invention, optionally dispersed in a resinous binder composition, and an aryl amine hole transport layer comprising aryl amine hole transport molecules optionally dispersed in a resinous binder.

Specific examples of perylene dimer pigments of the present invention, reference Formula 1, include those wherein R is hydrogen, methyl, ethyl, n-propyl, isopropyl, 3-methoxypropyl, 3-hydroxypropyl, cyclopropyl, cyclopropylmethyl, n-butyl, isobutyl, secbutyl, cyclobutyl, n-pentyl, 2-pentyl, 3-pentyl, 2-(3-methyl)butyl, 2-methylbutyl, 3-methylbutyl, neopentyl, cyclopentyl, n-hexyl, 2-ethylhexyl, cyclohexyl, n-heptyl, cycloheptyl, n-octyl, cyclooctyl, n-nonyl, n-decyl, n-undecyl, n-dodecyl, cyclododecyl, phenyl, benzyl, phenethyl and substituted phenyl, benzyl and phenethyl radicals or groups wherein the aromatic ring contains from 1 to 5 substituents inclusive of fluorine, chlorine, bromine, iodine, methyl, hydroxymethyl, trifluoromethyl, ethyl, tertiary-butyl, tertiary-butoxy, methoxy, trifluoromethoxy, nitro, cyano, dimethylamino, diethylamino, and the like. Specific examples of perylene dimer pigments of the present invention, reference Formula 2, include those wherein $R_1$ and $R_2$ are dissimilar and can be, for example, hydrogen, methyl, ethyl, n-propyl, isopropyl, 3-methoxypropyl, 3-hydroxypropyl, cyclopropyl, cyclopropylmethyl, n-butyl, isobutyl, secbutyl, cyclobutyl, n-pentyl, 2-pentyl, 3-pentyl, 2-(3-methyl)butyl, 2-methylbutyl, 3-methylbutyl, neopentyl, cyclopentyl, n-hexyl, 2-ethylhexyl, cyclohexyl, n-heptyl, cycloheptyl, n-octyl, cyclooctyl, n-nonyl, n-decyl, n-undecyl, n-dodecyl, cyclododecyl, phenyl, benzyl, phenethyl and substituted phenyl, benzyl and phenethyl radicals in groups in which the aromatic ring contains from 1 to 5 substituents inclusive of fluorine, chlorine, bromine, iodine, methyl, hydroxymethyl, trifluoromethyl, ethyl, tertiary-butyl, tertiary-butoxy, methoxy, trifluoromethoxy, nitro, cyano, dimethylamino, diethylamino, and the like.

More specifically, examples of the mixed perylenes of the present invention are comprised of mixed perylene dimers obtained from the condensation of a 1:1 mixture of n-pentylimidoperylene monoanhydride (Formula 3, R=n-pentyl) and 2-methylbutylimidoperylene monoanhydride (Formula 3, R=2-methylbutyl) with 1,3-diaminopropane. (The proportions of the three products are based on statistical calculations and on the assumption that both monoimides react at the same rate).

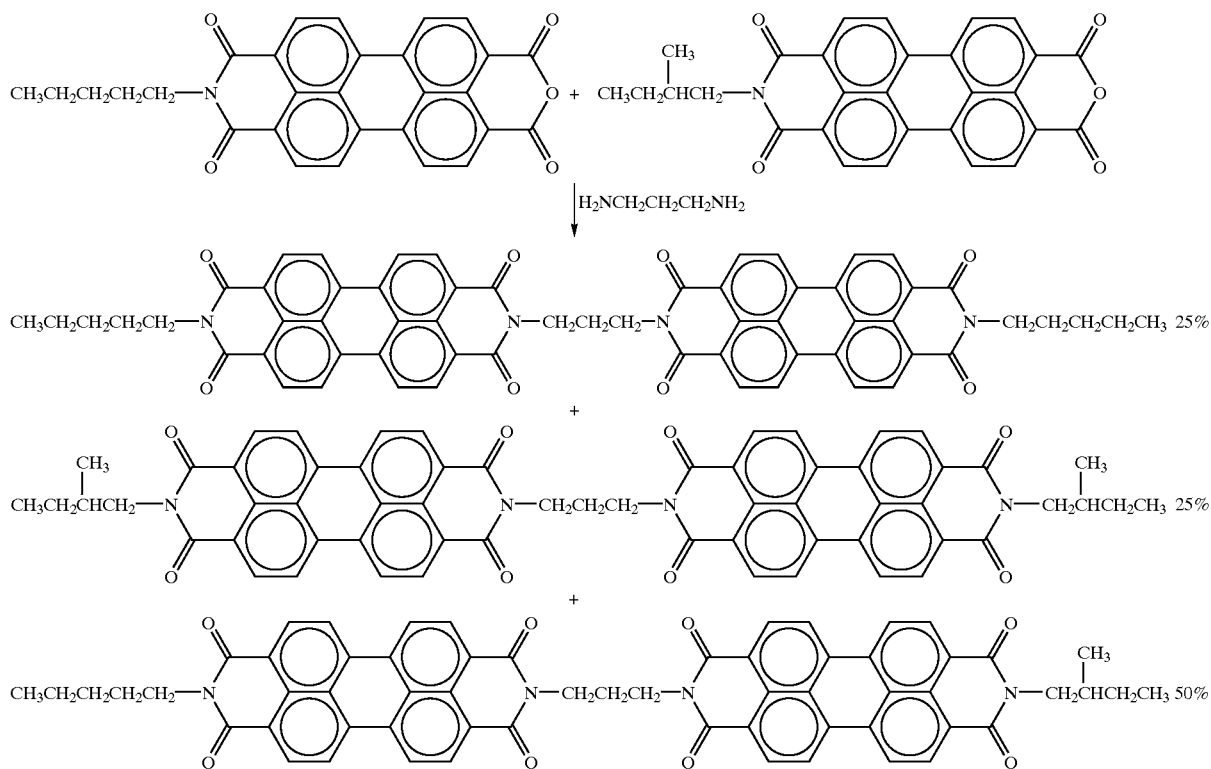

and the mixed perylene dimers that follow obtained from the condensation of a 1:1:1 mixture of n-pentylimidoperylene monoanhydride (Formula 3, R=n-pentyl), n-butylimidoperylene monoanhydride (Formula 3, R=n-butyl) and n-propylimidoperylene monoanhydride (Formula 3, R=n-propyl with 1,3-diaminopropane. (The proportions of the six products shown below are based upon statistical calculations and on the assumption that all three monoimides react at the same rate).

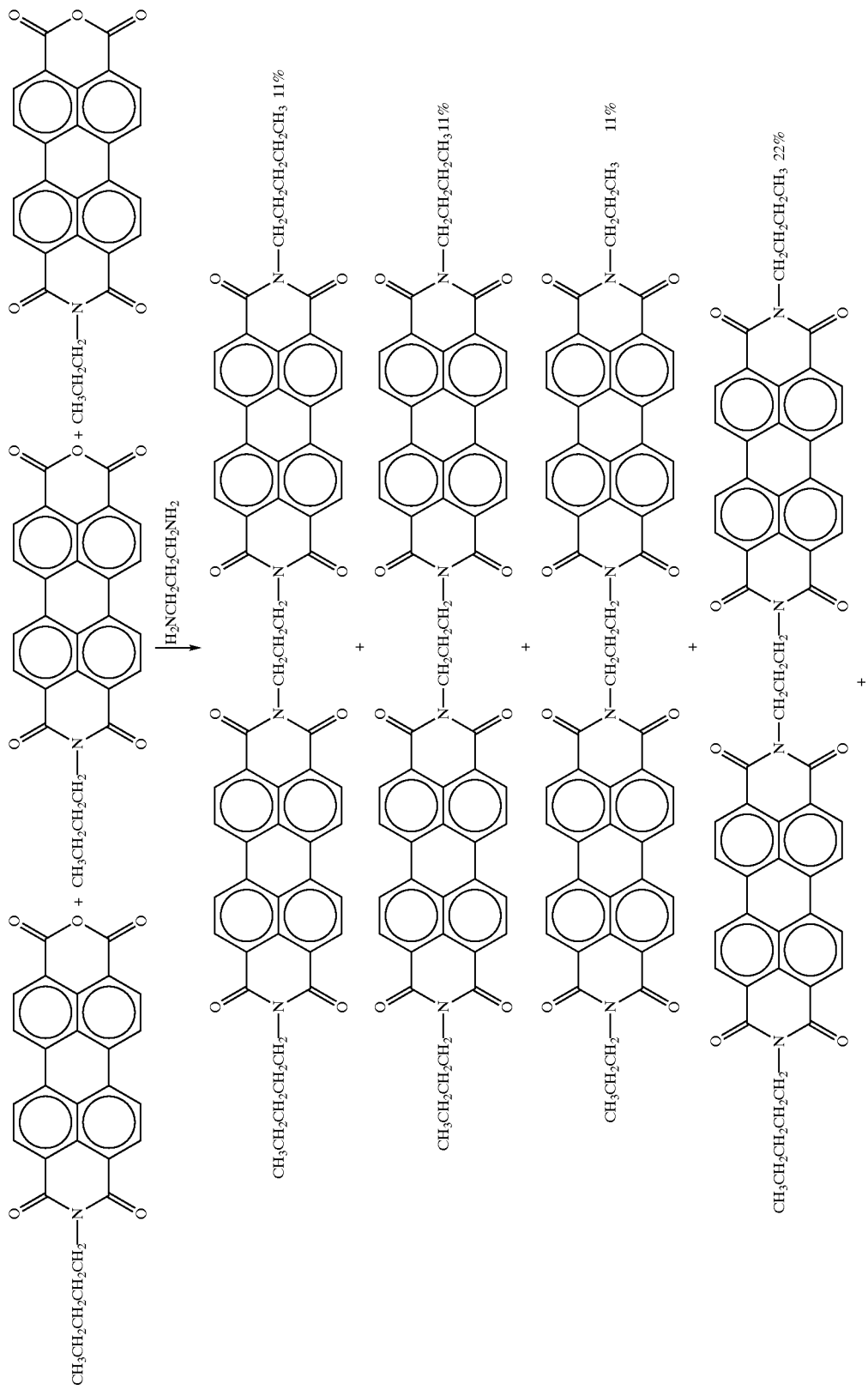

-continued
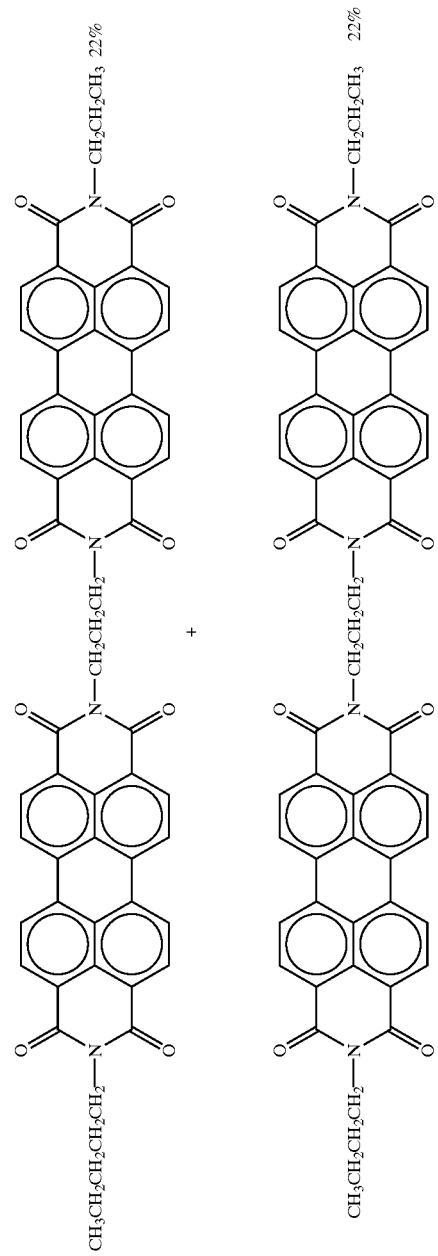

The processes of the present invention result in the formation of a mixture of different dimeric perylene bisimides, and it may be possible to accurately fully measure the amount of each component in a given mixture by, for example, nuclear magnetic resonance spectroscopy. However, simple statistical estimates of the composition can be made if, for example, it is assumed that the different monoimides all react with, for example, a diaminopropane and the intermediate aminopropyl bisimides at the same rate. To further illustrate this, only the R groups will be used to describe the different dimers represented by Formulae 1 and 2, that is, $R_n$-$R_n$ denotes the dimer of Formula 1 with two $R_n$ substituents, and $R_m$-$R_n$ denotes the unsymmetrical dimer of Formula 2 with different $R_m$ and Rn substituents.

Thus, for example, when a 1:1 mixture of two monoimides, corresponding to Formula 3, with $R_1$ and $R_2$ groups were condensed with diaminopropane, the product would be a mixture of 1 part (i.e. 25 percent) each of the two symmetric dimers, $R_1$-$R_1$ and $R_2$-$R_2$ and 2 parts (i.e. 50 percent) of the unsymmetrical dimer, $R_1$-$R_2$. For equal molar ratios of 3 different monoimides with $R_1$, $R_2$ and $R_3$ substituents, six different products would result: 1 part $R_1$-$R_1$, 1 part $R_2$-$R_2$, 1 part $R_3$-$R_3$, 2 parts $R_1$-$R_2$, 2 parts $R_1$-$R_3$ and 2 parts $R_2$-$R_3$. Similarly, for equimolar amounts of four different monoimides with $R_1$, $R_2$, $R_3$ and $R_4$ groups there would be 10 products: 1 part each of $R_1$-$R_1$, $R_2$-$R_2$, $R_3$-$R_3$ and $R_4$-$R_4$ and 2 parts each of $R_1$-$R_2$, $R_1$-$R_3$, $R_1$-$R_4$, $R_2$-$R_3$, $R_2$-$R_4$ and $R_3$-$R_4$. The prediction can be expressed mathematically as follows: the number of possible combinations that could form from equimolar amounts of n different monoimides with $R_1$, $R_2$, $R_3$ and the like to $R_n$ different substituents having similar reactivity would total $n^2$ with 1 part each of n symmetric dimers $R_n$-$R_n$ and 2 parts each of $(n^2-n)/2$ unsymmetrical dimers $R_m$-$R_n$. A similar statistical approach can be used to estimate the composition of dimers obtained from the condensation of nonequivalent amounts. For example, when a 2:1 mixture, respectively, of monoimides with $R_1$ and $R_2$ substituents were used, the product mixture would contain 9 different dimer combinations comprised of 4 parts of $R_1$-$R_1$, 1 part of $R_2$-$R_2$ and 4 parts of $R_1$-$R_2$. Similarly, a 6:4 ratio of monoimides having, respectively, an $R_1$ and $R_2$ substituent would lead to 100 possible combinations, 36 of which would be the $R_1$-$R_1$ dimer, 16 would be the $R_2$-$R_2$ dimer, and 48 would be the $R_1$-$R_2$ dimer.

Generally, the perylene bisimides of Formulas 1 and 2 can be prepared by the reaction of a mixture of monoimides of Formula 3 with a diamine. More specifically, the perylenes can be generated by the reaction of about two equivalents of monoimide-monoanhydride intermediate with one equivalent of a diamine, and wherein the intermediate can be prepared, generally illustrated as in U.S. Pat. No. 4,709,029, the disclosure of which is totally incorporated herein by reference, and H. Tooter, *Dyes and Pigments*, 4 (1983) 171–173, the disclosure of which is totally incorporated herein by reference, and more specifically, by the reaction of a primary amine R-$H_2$ wherein R is a suitable substituent, such as alkyl, and wherein the amine may be substituted with a mixture of two or more different amines with, for example, perylene-3,4,9,10-tetracarboxylic acid monoanhydride monopotassium salt. Mixed monoimide intermediates can be prepared by the reaction of a 50:50 mixture of n-pentyl amine and 2-methyl butyl amine when a mixture of two monoimides are selected the perylene mixture resulting is comprised of three compounds.

The mixed dimers of the present invention can be prepared by the condensation of a mixture of two or more monoimides of Formula 3, preferably with 1,3-diaminopropane, in a ratio of from about 1.5 to 4 molar equivalents of monoimide to 1 equivalent of the diamine in a high boiling solvent, such as dimethylformamide (DMF), decalin, sulfolane, imidazole or 1-methyl-2-pyrrolidinone (NMP) and the like, in a ratio of from about 1 to 55 parts monoimide (total weight of mixture) to about 100 parts (by weight) of solvent. The mixture can then be stirred under an inert atmosphere, such as nitrogen or argon gas, at a temperature of from about 100° C. to 250° C. for a suitable period of, for example, from about ½ to about 24 hours. The reaction mixture is then cooled to from about 25° C. to about 175° C., filtered and the separated solid is washed with from about 1 to about 10 portions of solvent inclusive of dimethylformamide (DMF), acetone, N-methylpyrrolidinone (NMP), methanol and water at a temperature of from about 25° C. to about 175° C., the portions of wash solvent being from about 10 percent to about 50 percent of the amount of solvent originally used to accomplish the condensation reaction. The washed product is then dried at a temperature of from about 50° C. to about 200° C. to provide the final mixed perylene photogenerating product.

In one process embodiment there is selected a ratio of from about 2 to about 2.5 equivalents of monoimide mixture to 1 equivalent of diaminopropane in a solvent, such as DMF (dimethyl formamide) or NMP, in an amount corresponding to about 10 to about 25 parts by weight of monoimide mixture to 100 parts of solvent and heating at a temperature of from about 155° C. to about 205° C. for a period of from about 1 to about 6 hours followed by cooling the reaction mixture to from about 90° C. to about 175° C., then filtering the hot mixture and washing the solid with 4 to 6 portions (such portions being in an amount corresponding to about 50 percent of the original reaction solvent) of DMF or NMP at a temperature of from about 90° C. to about 175° C., followed by from 1 to 4 similar portions of methanol and drying the resultant solid product at from about 60° C. to about 100° C. Optionally, water can be used in place of methanol in the final washing step and the pigment wet cake can be freeze dried. This process generally provides a fine, powdery pigment which is more readily dispersed in solvent than a solvent washed pigment which has been dried in an oven and that can sometimes result in the formation of a hard, caked mass of pigment which is difficult to disperse.

Optionally, the washed solid mixed dimer product can be stirred in a basic solution such as from about 1 to about 10 weight percent of an alkali metal hydroxide, such as potassium or sodium hydroxide in water at a temperature of from about 25° C. to about 100° C. for an effective period of, for example, from about 1 to about 72 hours followed by filtration and washing with water. This process serves to remove any residual unreacted monoimide, if present, by converting it to a deep purple-colored, water-soluble salt which salt is removed by washing the solid with water. A preferred base washing procedure selects from about 2 to about 5 percent by weight of aqueous potassium hydroxide solution at a temperature of from about 25° C. to about 80° C. for from about 2 to about 24 hours followed by filtration and washing the solid with water until the wash liquid is colorless.

The imaging substrate can be formulated entirely of an electrically conductive material, or it can be comprised of an insulating material having an electrically conductive surface. The substrate can be of an effective thickness, generally up to about 100 mils, and preferably from about 1 to about 50 mils, although the thickness can be outside of this range. The thickness of the substrate layer depends on many factors, including economic and mechanical considerations.

Thus, this layer may be of substantial thickness, for example over 100 mils, or of minimal thickness provided that there are no adverse effects thereof. In a particularly preferred embodiment, the thickness of this layer is from about 3 mils to about 10 mils. The substrate can be opaque or substantially transparent and can comprise numerous suitable materials having the desired mechanical properties. The entire substrate can comprise the same material as that in the electrically conductive surface, or the electrically conductive surface can merely be a coating on the substrate. Any suitable electrically conductive material can be employed. Typical electrically conductive materials include copper, brass, nickel, zinc, chromium, stainless steel, conductive plastics and rubbers, aluminum, semitransparent aluminum, steel, cadmium, titanium, silver, gold, paper rendered conductive by the inclusion of a suitable material therein or through conditioning in a humid atmosphere to ensure the presence of sufficient water content to render the material conductive, indium, tin, metal oxides, including tin oxide and indium tin oxide, and the like. The substrate layer can vary in thickness over substantially wide ranges depending on the desired use of the electrophotoconductive member. Generally, the conductive layer ranges in thickness of from about 50 Angstroms to centimeters, such as 100, although the thickness can be outside of this range. When a flexible electrophotographic imaging member is desired, the thickness typically is from about 100 Angstroms to about 750 Angstroms. The substrate can be of any other conventional material, including organic and inorganic materials. Typical substrate materials include insulating nonconducting materials, such as various resins known for this purpose including polycarbonates, polyamides, polyurethanes, paper, glass, plastic, polyesters such as MYLAR® (available from E. I. DuPont) or MELINEX 447® (available from ICI Americas, Inc.), and the like. If desired, a conductive substrate can be coated onto an insulating material. In addition, the substrate can comprise a metallized plastic, such as titanized or aluminized MYLAR®, wherein the metallized surface is in contact with the photogenerating layer or any other layer situated between the substrate and the photogenerating layer. The coated or uncoated substrate can be flexible or rigid, and can have any number of configurations, such as a plate, a cylindrical drum, a scroll, an endless flexible belt, or the like. The outer surface of the substrate preferably comprises a metal oxide such as aluminum oxide, nickel oxide, titanium oxide, and the like.

In embodiments, intermediate adhesive layers situated between the substrate and subsequently applied layers may be desirable to improve adhesion. When such adhesive layers are utilized, they preferably possess a dry thickness of from about 0.1 micron to about 5 microns, although the thickness can be outside of this range. Typical adhesive layers include film-forming polymers such as polyester, polyvinylbutyral, polyvinylpyrrolidone, polycarbonate, polyurethane, polymethylmethacrylate, and the like as well as mixtures thereof. Since the surface of the substrate can be a metal oxide layer or an adhesive layer, the expression substrate is intended to also include a metal oxide layer with or without an adhesive layer on a metal oxide layer. Moreover, other known layers may be selected for the photoconductive imaging members of the present invention, such as polymer protective overcoats, and the like.

The photogenerating layer is of an effective thickness, for example, of from about 0.05 micron to about 10 microns or more, and in embodiments has a thickness of from about 0.1 micron to about 3 microns. The thickness of this layer can be dependent primarily upon the concentration of photogenerating material in the layer, which may generally vary from about 5 to 100 percent. The 100 percent value generally occurs when the photogenerating layer is prepared by vacuum evaporation of the perylene pigment mixture. When the photogenerating material is present in a binder material, the binder contains, for example, from about 25 to about 95 percent by weight of the photogenerating material, and preferably contains about 60 to 80 percent by weight of the photogenerating material. Generally, it is desirable to provide this layer in a thickness sufficient to absorb about 90 to about 95 percent or more of the incident radiation, which is directed upon it in the imagewise or printing exposure step. The maximum thickness of this layer is dependent primarily upon factors such as mechanical considerations, such as the specific photogenerating compound selected, the thicknesses of the other layers, and whether a flexible photoconductive imaging member is desired.

Typical transport, especially hole transport, layers are described, for example, in U.S. Pat. Nos. 4,265,990; 4,609,605; 4,297,424 and 4,921,773, the disclosures of each of these patents being totally incorporated herein by reference. Organic charge transport materials can also be employed.

Hole transport molecules of the type described in U.S. Pat. Nos. 4,306,008; 4,304,829; 4,233,384; 4,115,116; 4,299,897; 4,081,274, and 5,139,910, the disclosures of each are totally incorporated herein by reference, can be selected for the imaging members of the present invention. Typical diamine hole transport molecules include N,N'-diphenyl-N, N'-bis(3-methylphenyl)-(1,1'-biphenyl)-4,4'-diamine, N,N'-diphenyl-N,N'-bis(4-methylphenyl)-(1,1'-biphenyl)-4,4'-diamine, N,N'-diphenyl-N,N'-bis(2-methylphenyl)-(1,1'-biphenyl)-4,4'-diamine, N,N'-diphenyl-N,N'-bis(3-ethylphenyl)-(1,1'-biphenyl)-4,4'-diamine, N,N'-diphenyl-N,N'-bis(4-ethylphenyl)-(1,1'-biphenyl)-4,4'-diamine, N,N'-diphenyl-N,N'-bis(4-n-butylphenyl)-(1,1'-biphenyl)-4,4'-diamine, N,N'-diphenyl-N,N'-bis(3-chlorophenyl)-(1,1'-biphenyl)-4,4'-diamine, N,N'-diphenyl-N,N'-bis(4-chlorophenyl)-(1,1'-biphenyl)-4,4'-diamine, N,N'-diphenyl-N,N'-bis(phenylmethyl)-(1,1'-biphenyl)-4,4'-diamine, N,N,N',N'-tetraphenyl-[2,2'-dimethyl-1,1'-biphenyl]-4,4'-diamine, N,N,N',N'-tetra-(4-methylphenyl)-[2,2'-dimethyl-1,1'-biphenyl]-4,4'-diamine, N,N'-diphenyl-N,N'-bis(4-methylphenyl)-[2,2'-dimethyl-1,1'-biphenyl]-4,4'-diamine, N,N'-diphenyl-N,N'-bis(2-methylphenyl)-[2,2'-dimethyl-1,1'-biphenyl]-4,4'-diamine, N,N'-diphenyl-N,N'-bis(3-methylphenyl)-[2,2'-dimethyl-1,1'-biphenyl]-4,4'-diamine, N,N'-diphenyl-N,N'-bis(3-methylphenyl)-pyrenyl-1,6-diamine, and the like.

A preferred hole transport layer, since it enables excellent effective transport of charges, is comprised of aryldiamine components as represented, or essentially represented, by the general formula of, for example, some of the U.S. patents indicated herein, wherein X and Y or X, Y and Z are selected from the group consisting of hydrogen, an alkyl group with, for example, from 1 to about 25 carbon atoms and a halogen, preferably chlorine, and at least one of X, Y and Z is independently an alkyl group or chlorine. When Y and Z are hydrogen, the compound may be N,N'-diphenyl-N,N'-bis-(alkylphenyl)-(1,1'-biphenyl)-4,4'-diamine wherein alkyl is, for example, methyl, ethyl, propyl, n-butyl, or the like, or the compound may be N,N'-diphenyl-N,N'-bis(chlorophenyl)-(1,1'-biphenyl)-4,4'-diamine.

The charge transport component is present in the charge transport layer in an effective amount, generally from about 5 to about 90 percent by weight, preferably from about 20 to about 75 percent by weight, and more preferably from about 30 to about 60 percent by weight, although the amount can be outside of this range.

Examples of the highly insulating and transparent resinous components or inactive binder resinous material for the transport layer include binders such as those described in U.S. Pat. No. 3,121,006, the disclosure of which is totally incorporated herein by reference. Specific examples of suitable organic resinous materials include polycarbonates, acrylate polymers, vinyl polymers, cellulose polymers, polyesters, polysiloxanes, polyamides, polyurethanes, polystyrenes, and epoxies as well as block, random or alternating copolymers thereof. A preferred electrically inactive binder is polycarbonate resins having a molecular weight of from about 20,000 to about 100,000 with a molecular weight ($M_w$) in the range of from about 50,000 to about 100,000 being particularly preferred. Generally, the resinous binder contains from about 5 to about 90 percent by weight of the active material corresponding to the foregoing formula, and preferably from about 20 percent to about 75 percent of this material.

Similar binder materials may be selected for the photogenerating layer, including polyesters, polyvinyl butyrals, polyvinylcarbazole, polycarbonates, polyvinyl formals, poly(vinylacetals) and those illustrated in U.S. Pat. No. 3,121,006, the disclosure of which is totally incorporated herein by reference.

The photoconductive imaging member may optionally contain a charge blocking layer situated between the conductive substrate and the photogenerating layer. This layer may comprise metal oxides, such as aluminum oxide and the like, or materials such as silanes and nylons. Additional examples of suitable materials include polyisobutyl methacrylate, copolymers of styrene and acrylates such as styrene/n-butyl methacrylate, copolymers of styrene and vinyl toluene, polycarbonates, alkyl substituted polystyrenes, styrene-olefin copolymers, polyesters, polyurethanes, polyterpenes, silicone elastomers, mixtures thereof, copolymers thereof, and the like. The primary purpose of this layer is to prevent charge injection from the substrate during and after charging. This layer is of a thickness of less than 50 Angstroms to about 10 microns, preferably being no more than about 2 microns.

The present invention also encompasses a method of generating images with the photoconductive imaging members disclosed herein. The method comprises, for example, generating an electrostatic latent image on a photoconductive imaging member of the present invention, developing the latent image with a toner comprised of resin, pigment like carbon black, and a charge additive, and transferring the developed electrostatic image to a substrate. Optionally, the transferred image can be permanently affixed to the substrate. Development of the image may be achieved by a number of methods, such as cascade, touchdown, powder cloud, magnetic brush, and the like. Transfer of the developed image to a substrate, such as paper, may be by any suitable method, including those wherein there is selected a corotron or a biased roll. Fixing step may be performed by any suitable method, such as flash fusing, heat fusing, pressure fusing, vapor fusing, and the like. Any substrate selected for xerographic copiers and printers, including digital copiers, may be used as a substrate, such as paper, transparency material, and the like.

Specific embodiments will now be described in detail. These Examples are intended to be illustrative, and are not limited to the materials, conditions, or process parameters set forth. All parts and percentages are by weight unless otherwise indicated. Comparative Examples are also provided.

SYNTHESIS EXAMPLES

The starting monoanhydride monoimides (Formula 3) in the following Examples were prepared by the methods described in U.S. Pat. No. 4,501,906, the disclosure of which is totally incorporated herein by reference, or by minor adaptations of the processes described therein. The structures or formula of the mixed dimers were mainly established by $^1H$ and $^{13}C$ nuclear magnetic resonance spectrometry in solvent mixtures containing trifluoroacetic acid. Visible absorption spectra in trifluoroacetic acid-methylene chloride solution were also measured for each product. The bisimide dimers evidence solution absorbence maxima at about 500 and 540 nanometers, which is diagnostic for the perylene bisimide chromophore in the solution solvent system. The nomenclature to fully adequately describe the reagents and products of the following Examples can be complicated. Therefore, to avoid or minimize confusion and ambiguity, the compounds are described in relation to Formulae 1, 2 and 3.

The synthesis Examples that follow are representative of the general synthesis and purification processes selected.

SYNTHESIS EXAMPLE 1

Condensation of a 60:40 Mixture of n-Pentylimidoperylene Monoanhydride (Formula 3, R=N-pentyl) and 2-methylbutylimido Perylene Monoanhydride with 1,3-Diaminopropane A mixture of n-pentylimidoperylene monoanhydride (Formula 3, R=n-pentyl, 5.53 grams, 0.012 mole) and 2-methylbutylimidoperylene monoanhydride (Formula 3, R=2-methylbutyl, 3.69 grams, 0.008 mole) in 450 milliliters of 1-methyl-2-pyrrolidinone (NMP) was treated with 1,3-diaminopropane (0.667 gram, 0.751 milliliter, 0.0090 mole). The mixture was stirred at room temperature, about 25° C. to about 30° C., for 30 minutes then was heated to reflux (202° C.) for 70 minutes. The resultant black suspension was cooled by stirring at ambient temperature to 150° C. and was then filtered. The resulting solid was washed with 4×100 milliliter portions of boiling N,N-dimethylformamide (DMF), followed by 25 milliliters of cold DMF and 4×25 milliliters portions of methanol. The product was dried at 60° C. to provide 8.2 grams (95 percent yield) of a black solid. The proton magnetic resonance spectrum of this product indicated that it was comprised of a mixture of about 36 percent of the dimer corresponding to Formula 1 with R=n-pentyl, 16 percent of the dimer corresponding to Formula 1 with R=2-methylbutyl, and 48 percent of the dimer corresponding to Formula 2 with $R_1$=n-pentyl and $R_2$=2-methylbutyl.

SYNTHESIS EXAMPLE 2

Condensation of a 1:1 Mixture of n-Butylimidoperylene Monoanhydride (Formula 3, R=n-Butyl) and n-Hexylimidoperylene Monoanhydride (Formula 3, R=n-Hexyl) with 1,3-Diaminopropane Mono-n-butylimidoperylene monoanhydride (1.23 grams, 0.00275 mole) and mono-n-hexylimidoperylene monoanhydride (1.31 grams, 0.00275 mole) were stirred in 150 milliliters of NMP for 30 minutes at room temperature. 1,3-Diaminopropane (0.185 gram, 209 µL, 0.00250 mole) was added and the resulting mixture was stirred for 30 minutes at room temperature, about 25° C., then was heated at reflux for 1 hour. The mixture resulting was then cooled to 150° C. and was filtered. The resulting solid was washed with 4×50 milliliter portions of boiling DMF (dimethyl formamide) then with 20 milliliters of cold DMF followed by 2×20 milliliters of water. The wet cake resulting was vigorously stirred in 200 milliliters of water containing 2 grams of potassium hydroxide for 18 hours. The product was then filtered and the solid was washed with 5×100 milliliter portions of water followed by 3×25 milliliter portions of methanol. Drying at 60° C. provided 2.2 grams (92 percent) of a jet-black powder. The proton magnetic resonance spectrum of this product indicated that it was comprised of a mixture of about 25 percent of the dimer corresponding to Formula 1 with R=n-butyl, 25 percent of the dimer corresponding to Formula 1 with R=n-hexyl, and 50 percent of the dimer corresponding to Formula 2 with $R_1$=n-butyl and $R_2$=n-hexyl.

SYNTHESIS EXAMPLE 3
Condensation of a 1:1 Mixture of n-Butylimidoperylene Monoanhydride (Formula 3, R=n-Butyl) and n-Pentylimidoperylene Monoanhydride (Formula 3, R=n-Pentyl) with 1,3-Diaminopropane The synthesis and purification procedures of Example 2 were repeated using n-pentylimidoperylene monoanhydride (1.27 grams) in place of the n-hexylimido anhydride, thereby providing 2.3 grams of crude product, which after base purification provided 2.2 grams (93 percent) of a black powder. The proton magnetic resonance spectrum of this product indicated that it was comprised of a mixture of about 25 percent of the dimer corresponding to Formula 1 with R=n-butyl, 25 percent of the dimer corresponding to Formula 1 with R=n-pentyl, and 50 percent of the dimer corresponding to Formula 2 with $R_1$=n-butyl and $R_2$=n-pentyl.

SYNTHESIS EXAMPLE 4
Condensation of a 1:1 Mixture of Isobutylimidoperylene Monoanhydride (Formula 3, R=Isobutyl) and n-Pentylimidoperylene Monoanhydride (Formula 3, R=n-Pentyl) with 1,3-Diaminopropane The synthesis and purification procedures of Example 3 were repeated using isobutylimidoperylene monoanhydride (1.23 grams) in place of the n-butylmonoimide monoanhydride, thus providing 2.1 grams (89 percent) of black solid after base purification. The proton magnetic resonance spectrum of this product indicated that it was comprised of a mixture of about 25 percent of the dimer corresponding to Formula 1 with R=isobutyl, 25 percent of the dimer corresponding to Formula 1 with R=n-pentyl, and 50 percent of the dimer corresponding to Formula 2 with $R_1$=isobutyl and $R_2$=n-pentyl.

SYNTHESIS EXAMPLE 5
Condensation of a 1:1:1 Mixture of n-Butylimidoperylene Monoanhydride (Formula 3, R=n-Butyl), n-Pentylimidoperylene Monoanhydride (Formula 3, R=n-Pentyl) and 2-Methylbutylimido perylene Monoanhydride (Formula 3, R=2-Methylbutyl) with 1,3-Diaminopropane A stirred mixture of n-butylimidoperylene monoanhydride (1.12 grams, 0.0025 mole), n-pentylimidoperylene monoanhydride (1.15 grams, 0.0025 mole) and 2-methylbutylimidoperylene monoanhydride (1.15 grams, 0.0025 mole) in 150 milliliters of NMP was treated with 1,3-diaminopropane (292 μL, 0.0035 mole). The mixture resulting was heated at reflux (202° C.) for 2 hours, then was cooled to about 150° C. and was filtered. The solid was washed with boiling DMF followed by cold DMF, then methanol as in the above Examples, then was dried to provide 3.15 grams (94 percent) of a black solid. The proton magnetic resonance spectrum of this product indicated that it was comprised of a mixture of 6 compounds composed of about 11 percent of the dimer corresponding to Formula 1 with R=n-butyl, 11 percent of the dimer corresponding to Formula 1 with R=n-pentyl, 11 percent of the dimer corresponding to Formula 1 with R=2-methylbutyl, 22 percent of the dimer corresponding to Formula 2 with $R_1$=n-butyl and $R_2$=n-pentyl, 22 percent of the dimer corresponding to Formula 2 with $R_1$=n-butyl and $R_2$=2-methylbutyl and 22 percent of the dimer corresponding to Formula 2 with $R_1$=n-pentyl and $R_2$=2-methylbutyl.

SYNTHESIS EXAMPLE 6
Condensation of a 2:1:1 Mixture, Respectively, of n-Butylimidoperylene Monoanhydride (Formula 3, R=n-Butyl), n-Pentylimidoperylene Monoanhydride (Formula 3, R=n-Pentyl) and 2-methylbutylimido perylene Monoanhydride (Formula 3, R=2-Methylbutyl) with 1,3-Diaminopropane A stirred mixture of n-butylimidoperylene monoanhydride (2.24 grams, 0.0050 mole), n-pentylimidoperylene monoanhydride (1.15 grams, 0.0025 mole) and 2-methylbutylimidoperylene monoanhydride (1.15 grams, 0.0025 mole) in 175 milliliters of NMP was treated with 1,3-diaminopropane (376 μL, 0.0045 mole). The mixture was heated at reflux (202° C.) for 2 hours, then was cooled to about 150° C. and was filtered. The resulting solid was washed with boiling DMF followed by cold DMF then methanol as in the above Examples, then was dried to provide 4.06 grams (95 percent) of the perylene pigment mixture as a black solid. The proton magnetic resonance spectrum of this product indicated that it was comprised of a mixture of 6 compounds composed of about 4 parts of the dimer corresponding to Formula 1 with R=n-butyl, 1 part of the dimer corresponding to Formula 1 with R=n-pentyl, 1 part of the dimer corresponding to Formula 1 with R=2-methylbutyl, 4 parts of the dimer corresponding to Formula 2 with $R_1$=n-butyl and $R_2$=n-pentyl, 4 parts of the dimer corresponding to Formula 2 with $R_1$=n-butyl and $R_2$=2-methylbutyl and 2 parts of the dimer corresponding to Formula 2 with $R_1$=n-pentyl and $R_2$=2-methylbutyl.

SYNTHESIS EXAMPLE 7
Condensation of a 1:2:1 Mixture, Respectively, of n-Butylimidoperylene Monoanhydride (Formula 3, R=n-Butyl), n-Pentylimidoperylene Monoanhydride (Formula 3, R=n-Pentyl) and 2-Methylbutylimido Perylene Monoanhydride (Formula 3, R=2-Methylbutyl) with 1,3-Diaminopropane A stirred mixture of n-butylimidoperylene monoanhydride (1.12 grams, 0.0025 mole), n-pentylimidoperylene monoanhydride (2.30 grams, 0.0050 mole) and mono(2-methylbutylimido)perylene monoanhydride (1.15 grams, 0.0025 mole) in 175 milliliters of NMP was treated with 1,3-diaminopropane (376 μL, 0.0045 mole). The mixture was heated at reflux (202° C.) for 2 hours, then was cooled to about 150° C. and was filtered. The solid resulting was washed with boiling DMF followed by cold DMF, then methanol as in the above Examples, then was dried to provide 4.01 grams (94 percent) of the perylene pigment mixture as a black solid. The proton magnetic resonance spectrum of this product indicated that it was a mixture comprised of 6 compounds of about 1 part of the dimer corresponding to Formula 1 with R=n-butyl, 4 parts of the dimer corresponding to Formula 1 with R=n-pentyl, 1 part of the dimer corresponding to Formula 1 with R=2-methylbutyl, 2 parts of the dimer corresponding to Formula 2 with $R_1$=n-butyl and $R_2$=n-pentyl, 4 parts of the dimer corresponding to Formula 2 with $R_1$=n-butyl and $R_2$=2-methylbutyl and 4 parts of the dimer corresponding to Formula 2 with $R_1$=n-pentyl and $R_2$=2-methylbutyl.

SYNTHESIS EXAMPLE 8

Condensation of a 1:1:1 Mixture of n-Propylimidoperylene Monoanhydride (Formula 3, R=n-Propyl), n-Pentylimidoperylene Monoanhydride (Formula 3, R=n-Pentyl) and n-Heptylimidoperylene Monoanhydride (Formula 3, R=n-Heptyl) with 1,3-Diaminopropane A stirred mixture of n-propylimidoperylene monoanhydride (1.08 grams, 0.0025 mole), n-pentylimidoperylene monoanhydride (1.15 grams, 0.0025 mole) and n-heptylimidoperylene monoanhydride (1.22 grams, 0.0025 mole) in 150 milliliters of NMP was treated with 1,3-diaminopropane (0.259 gram, 292 µL, 0.0035 mole) The mixture was heated at reflux (202° C.) for 1 hour, then was cooled to 160° C. and was filtered. The solid was washed with 4×50 milliliters portions of boiling DMF followed by 3×20 milliliter portions of methanol and then it was dried to provide 3.1 grams (94 percent) of a black solid. The proton magnetic resonance spectrum of this product indicated that it was a mixture comprised of 6 compounds of about 11 percent of the dimer corresponding to Formula 1 with R=n-propyl, 11 percent of the dimer corresponding to Formula 1 with R=n-pentyl, 11 percent of the dimer corresponding to Formula 1 with R=n-heptyl, 22 percent of the dimer corresponding to Formula 2 with R$_1$=n-propyl and R$_2$=n-pentyl, 22 percent of the dimer corresponding to Formula 2 with R$_1$=n-propyl and R$_2$=n-heptyl, and 22 percent of the dimer corresponding to Formula 2 with R$_1$=n-pentyl and R$_2$=n-heptyl.

SYNTHESIS EXAMPLE 9

Condensation of a 1:1:1 Mixture, Respectively, of n-Butylimidoperylene Monoanhydride (Formula 3, R=n-Butyl), Neopentylimidoperylene Monoanhydride (Formula 3, R=Neopentyl) and Benzylimidoperylene Monoanhydride (Formula 3, R=Benzyl) with 1,3-Diaminopropane A stirred mixture of n-butylimidoperylene monoanhydride (1.12 grams, 0.0025 mole), neopentylimidoperylene monoanhydride (1.15 grams, 0.0025 mole) and mono(benzylimido)perylene monoanhydride (1.20 grams, 0.0025 mole) in 150 milliliters of NMP was treated with 1,3-diaminopropane (292 µL, 0.0035 mole). The mixture was heated at reflux (202° C.) for 1 hour, then was cooled to about 150° C. and was filtered. The solid was washed with 4×50 milliliter portions of boiling DMF followed by cold DMF, then methanol as in the above Example, then was dried to provide 3 grams (88 percent) of a black solid. The proton magnetic resonance spectrum of this product indicated that it was a mixture comprised of 6 compounds of about 11 percent of the dimer corresponding to Formula 1 with R=n-butyl, 11 percent of the dimer corresponding to Formula 1 with R=neopentyl, 11 percent of the dimer corresponding to Formula 1 with R=benzyl, 22 percent of the dimer corresponding to Formula 2 with R$_1$=n-butyl and R$_2$=neopentyl, 22 percent of the dimer corresponding to Formula 2 with R$_1$=n-butyl and R$_2$=benzyl and 22 percent of the dimer corresponding to Formula 2 with R$_1$=neopentyl and R$_2$=benzyl.

SYNTHESIS EXAMPLE 10

Condensation of a 1:1:1:1 Mixture of n-Propylimidoperylene Monoanhydride (Formula 3, R=n-Propyl), n-Butylimidoperylene Monoanhydride (Formula 3, R=n-Butyl) n-Pentylimidoperylene Monoanhydride (Formula 3, R=n-Pentyl) and n-Octylimidoperylene Monoanhydride (Formula 3, R=n-Octyl) with 1,3-Diaminopropane A stirred mixture of n-propylimidoperylene monoanhydride (1.20 grams (0.00275 mole), n-butylimidoperylene monoanhydride (1.23 grams, 0.00275 mole), n-pentylimidoperylene monoanhydride (1.27 grams, 0.00275 mole) and n-octylimidoperylene monoanhydride (1.38 grams, 0.00275 mole) in 300 milliliters of NMP was treated with 1,3-diaminopropane (0.371 gram, 417 µL, 0.0050 mole). The mixture was heated at reflux (202° C.) for 1¼ hours, then was cooled to 160° C. and was filtered. The solid was washed with 3×100 milliliter portions of boiling DMF followed by 3×20 milliliters of methanol, then was dried to provide 4.4 grams (92 percent) of a black solid (perylene mixture). The proton magnetic resonance spectrum of this product indicated that it was comprised of a mixture of 10 compounds composed of about 1 part of the dimer corresponding to Formula 1 with R=n-propyl, 1 part of the dimer corresponding to Formula 1 with R=n-butyl, 1 part of the dimer corresponding to Formula 1 with R=n-pentyl, 1 part of the dimer corresponding to Formula 1 with R=n-octyl, 2 parts of the dimer corresponding to Formula 2 with R$_1$=n-propyl and R$_2$=n-butyl, 2 parts of the dimer corresponding to Formula 2 with R$_1$=n-propyl and R$_2$=n-pentyl, 2 parts of the dimer corresponding to Formula 2 with R$_1$=n-propyl and R$_2$=n-octyl, 2 parts of the dimer corresponding to Formula 2 with R$_1$=n-butyl and R$_2$=n-pentyl, 2 parts of the dimer corresponding to Formula 2 with R$_1$=n-butyl and R$_2$=n-octyl, and 2 parts of the dimer corresponding to Formula 2 with R$_1$=n-pentyl and R$_2$=n-octyl.

Comparative Synthesis Example 1

Synthesis of the Bis(n-Pentyl) Symmetric Dimer. Formula 1, R=n-Pentyl

The compound (n-pentylimido)perylene monoanhydride, Formula 3, R=n-pentyl, (20.3 grams, 0.044 mole) was stirred under an argon atmosphere in 1,250 milliliters of NMP. 1,3-Diaminopropane (1.483 grams, 1.67 milliliters, 0.020 mole) was added and the mixture was stirred at room temperature for 15 minutes, then was heated to reflux (ca. 202° C.) for 2 hours. The resultant black suspension was cooled to 160° C. and was filtered. The solid was washed with 4×400 milliliters portions of boiling DMF, then with 200 milliliters of cold DMF and 2×100 milliliters portions of methanol. The product was dried at 60° C. to provide 17.8 grams (93 percent yield) of a fine black powder.

Comparative Synthesis Example 2

Synthesis of the Bis(2-methylbutyl) Symmetric Dimer. Formula 1, R=2-Methylbutyl

A dispersion of 5.07 grams (0.011 mole) of 2-methyl butylimido)perylene monoanhydride (Formula 3, R=2-methylbutyl) in 300 milliliters of NMP was treated with 0.371 gram (417 µL, 0.0050 mole) of 1,3-diamino propane. The mixture was stirred at room temperature under argon for 15 minutes, then was heated to reflux (202° C.) for 2 hours. The mixture was cooled to 155° C. and was filtered and washed with 3×100 milliliter portions of boiling DMF, then with 50 milliliters of cold DMF followed by 3×25 milliliter portions of methanol. The product was dried at 60° C. to provide 4.55 grams (95 percent yield) of a fine brown solid.

Comparative Synthesis Example 3

Synthesis of the Pure Unsymmetrical n-Pentyl-2-Methylbutyl Dimer. Formula 2, R$_1$=n-Pentyl, R$_2$=2-Methylbutyl A mixture of n-pentylimido perylene monoanhydride (Formula 3, R=n-pentyl, 2.31 grams, 0.0050 mole) and the acetate salt of 2-methylbutylimido-3-aminopropylimido-perylene (prepared as described in copending application U.S. Ser. No. 09/165,595, the disclosure of which is totally incorporated herein by reference, 2.60 grams, 0.045 mole) was stirred in 300 milliliters of NMP, then was heated to reflux for 1 hour. The mixture was cooled to 150° C. and was filtered. The resulting solid was washed with 3×50 milliliters portions of boiling DMF followed by 2×10 milliliter portions of methanol. The wet cake resulting was stirred vigorously in 125 milliliters of water containing 2 grams of potassium hydroxide for 16 hours. Filtration, washing with 4×100 milliliter portions of boiling water and 2×25 milliliter portions of methanol and drying at 60° C. provided 3.7 grams (87 percent yield) of the above terminally unsymmetrical dimer.

Comparative Synthesis Example 4
Synthesis of the Bis(n-butyl) Symmetric Dimer. Formula 1, R=n-Butyl The compound n-butylidoperylene monoanhydride (Formula 3, R=n-butyl, 3.93 grams, 0.0088 mole) was stirred under an argon atmosphere in 200 milliliters of NMP. 1,3-Diaminopropane (0.296 gram, 0.334 milliliter, 0.0040 mole) was added and the mixture was stirred at room temperature for 15 minutes, then was heated to reflux (202° C.) for 3 hours. The resultant black suspension was cooled to 155° C. and was then filtered. The solid resulting was washed with 4×50 milliliter portions of boiling DMF then with 50 milliliters of cold DMF and 3×50 milliliter portions of methanol. The product was dried at 60° C. to provide 3.4 grams (92 percent yield) of a fine black powder.

Comparative Synthesis Example 5
Synthesis of the Bis(n-hexyl) Symmetric Dimer. Formula 1, R=n-Hexyl n-Hexylimidoperylene monoanhydride (Formula 3, R=n-hexyl, 4.18 grams, 0.0088 mole) was stirred under an argon atmosphere in 200 milliliters of NMP. 1,3-Diaminopropane (0.296 gram, 0.334 milliliter, 0.0040 mole) was added and the mixture was stirred at room temperature for 15 minutes, then was heated to reflux (202° C.) for 3 hour. The resultant black suspension was cooled to 155° C. and was filtered. The solid resulting was washed with 4×50 milliliter portions of boiling DMF then with 50 milliliters of cold DMF and 3×50 milliliter portions of methanol. The product was dried at 60° C. to provide 3.7 grams (94 percent yield) of a black solid.

Comparative Synthesis Example 6
Synthesis of the Pure Unsymmetrical n-butyl-n-hexyl Dimer. Formula 2, $R_1$=n-Pentyl, $R_2$=2-Methylbutyl A mixture of n-hexylimidoperylene monoanhydride (Formula 3, R=n-hexyl, 2.37 grams, 0.0050 mole) and the acetate salt of n-butylimido-3-aminopropylimido-perylene (prepared as described in copending application U.S. Ser. No. 09/165,595, 2.02 grams, 0.040 mole) in 200 milliliters of NMP was stirred and heated to reflux for 1½ hour. The mixture was cooled to 155° C. and was filtered. The solid was washed with 3×75 milliliter portions of boiling DMF followed by 3×20 milliliter portions of methanol. The product was stirred vigorously in 100 milliliters of water containing 2 grams of potassium hydroxide for 48 hours. Filtration, washing with 2×100 milliliter portions of water followed by 2×50 milliliter portions of boiling water and 2×20 milliliter portions of methanol, and drying at 60° C. provided 2.9 grams (76 percent yield) of the above terminally unsymmetrical dimer.

Xerographic Evaluation of Perylene Bisimide Dimer Mixtures

Photoresponsive imaging members were fabricated with the unsymmetrical perylene dimer pigments obtained by Synthesis Examples 1 to 10 and Comparative Synthesis Examples 1 to 6. These photoresponsive, or photoconductive imaging members are generally known as dual layer photoreceptors containing a photogenerator layer, and thereover a charge transport layer. The photogenerator layer was prepared from a pigment dispersion as follows: 0.2 gram of the perylene dimer pigment was mixed with 0.05 gram of polyvinylcarbazole (PVK) polymer and 8.1 milliliters of methylene chloride in a 30 milliliter glass bottle containing 70 grams of ⅛ inch stainless steel balls. The bottle was placed on a roller mill and the dispersion was milled for 4 days. Using a film applicator of 1.5 mil gap, the pigment dispersion was coated to form the photogenerator layer on a titanized MYLAR® substrate of 75 microns in thickness, which had a gamma amino propyl triethoxy silane layer, 0.1 micron in thickness, thereover, and E. I. DuPont 49,000 polyester adhesive thereon in a thickness of 0.1 micron. Thereafter, the photogenerator layer formed was dried in a forced air oven at 135° C. for 20 minutes. Photogenerator layers for each photoconductive member were each overcoated with an amine charge transport layer prepared as follows. A transport layer solution was made by mixing 8.3 grams of MAKROLON™, a polycarbonate resin, 4.4 grams of N,N'-diphenyl-N,N'-bis(3-methylphenyl)-(1,1'-biphenyl)-4,4'-diamine and 82.3 grams of methylene chloride. The solution was coated onto the above photogenerating layer using a film applicator of 10 mil gap. The resulting members were dried at 135° C. in a forced air oven for 20 minutes. The final dried thickness of transport layer was 20 microns.

The xerographic electrical properties of each imaging member were then determined by electrostatically charging its surface with a corona discharging photoconductive member until the surface potential, as measured by a capacitively coupled probe attached to an electrometer, attained an initial value $V_o$=800 volts. After resting for 0.5 second in the dark, the charged member reached a surface potential of $V_{ddp}$, dark development potential, and was then exposed to light from a filtered xenon lamp. A reduction in the surface potential to $V_{bg}$, background potential due to photodischarge effect, was observed. The dark decay in volt/second was calculated as $(V_o - V_{ddp})/0.5$. The lower the dark decay value, the superior is the ability of the member to retain its charge prior to exposure by light. Similarly, the lower the $V_{ddp}$, the poorer is the charging behavior of the member. The percent photodischarge was calculated as 100 percent× $(V_{ddp} - V_{bg})V_{ddp}$. The light energy used to photodischarge the imaging member during the exposure step was measured with a light meter. The photosensitivity of the imaging member can be described in terms of $E_{1/2}$, amount of exposure energy in erg/cm$^2$ required to achieve 50 percent photodischarge from the dark development potential. The higher the photosensitivity, the smaller the $E_{1/2}$ value. High-photosensitivity (lower $E_{1/2}$ value), lower dark decay and high charging are desired for the improved performance of xerographic imaging members.

The following Table 1 summarizes the xerographic electrical results obtained for photoconductive members made with the 10 Example pigments. The exposure light used was at a wavelength of 620 nanometers.

TABLE 1

Photosensitivities of Mixed Dimeric Perylene Bisimides

| Synthesis Example | Dark Decay [500 ms] (V) | $E_{1/2}$ (ergs/cm$^2$) | $V_r$ (-V) |
|---|---|---|---|
| 1 | 45.1 | 2.28 | 2 |
| 2 | 41.9 | 2.51 | 2 |
| 3 | 51.3 | 2.86 | 4 |
| 4 | 89.1 | 2.71 | 13 |
| 5 | 102.4 | 2.57 | 5 |
| 6 | 89.8 | 2.50 | 6 |
| 7 | 71.9 | 2.43 | 3 |
| 8 | 47.1 | 2.93 | 2 |
| 9 | 92.6 | 3.13 | 6 |
| 10 | 48.3 | 2.98 | 2 |

All the imaging members with the invention mixed dimeric photogenerating pigments (Synthesis Examples 1 to 10) exhibited acceptable charge acceptance of 800 volts, and most showed a dark decay of from about 40 to about 100 volts per second. All exhibited excellent photosensitivities ranging from $E_{1/2}$=2.28 to 3.13 ergs/cm$^2$.

le;.5qThere does not appear to be an exacting empirical or theoretical correlation between the composition or structures of these perylene pigment dimer mixtures and their efficacy as photogenerator pigments for xerographic imaging applications. However, it was found that a number of the invention mixed dimeric perylene bisimides possessed enhanced photosensitivities compared to some of the pure dimeric perylene bisimide pigments described, for example, in U.S. Pat. Nos. 5,645,965; 5,683,842 and copending application U.S. Ser. No. 09/165,595.

This is illustrated by reference to Table 2, which compares the photosensitivities of photoconductive members prepared from the mixed pigment compositions of Synthesis Examples 1 and 2 with the sensitivities obtained using the individual components present in the mixture. The n-pentyl-2-methylbutyl mixed dimer pigment prepared as described above (Synthesis Example 1) provided an imaging member with a sensitivity $E_{1/2}$ of 2.28 Ergs/cm$^2$. The corresponding pure n-pentyl dimer (Formula 1, R=n-pentyl, Comparative Synthesis Example 1) provided 2.85, the pure 2-methylbutyl dimer (Formula 1, R=2-methylbutyl, Comparative Synthesis Example 2) provided 5.45 and the terminally unsymmetrical dimer (Formula 2 with $R_1$=n-pentyl and $R_2$=2-methylbutyl, Comparative synthesis Example 3) 3.33 Ergs/cm$^2$. Similarily, the n-butyl-n-hexyl mixed dimer pigment prepared as described above (Synthesis Example 2) provided an imaging member with a sensitivity $E_{1/2}$ of 2.51 Ergs/cm$^2$. The corresponding pure bis-n-butyl dimer (Formula 1, R=n-butyl, Comparative Synthesis Example 4) provided 2.85, the pure n-hexyl dimer (Formula 1, n-hexyl, Comparative Synthesis Example 5) provided 4.34, and the terminally unsymmetrical dimer (Formula 2 with $R_1$=n-butyl and $R_2$=n-hexyl, Comparative Synthesis Example 6) 2.73 Ergs/cm$^2$.

TABLE 2

Photosensitivities of Mixed and Pure Dimeric Perylene Bisimides

| Synthesis Example | Comparative Synthesis Example | Dark Decay [500 ms] (V) | $E_{1/2}$ (ergs/cm$^2$) | $V_r$ (-V) |
|---|---|---|---|---|
| 1 |   | 45.1 | 2.28 | 2 |
|   | 1 | 51.9 | 2.85 | 2 |
|   | 2 | 20.0 | 5.45 | 3 |
|   | 3 | 52.4 | 3.33 | 4 |
| 2 |   | 41.9 | 2.51 | 2 |
|   | 4 | 29.5 | 4.69 | 4 |
|   | 5 | 29.8 | 4.34 | 6 |
|   | 6 | 62.5 | 2.73 | 4 |

Other embodiments and modifications of the present invention may occur to those skilled in the art subsequent to a review of the information presented herein; these embodiments, modifications, and equivalents thereof, are also included within the scope of the present invention.

What is claimed is:

1. A process for the preparation of perylene mixtures comprised of at least two symmetrical perylene bisamide dimers of Formula 1

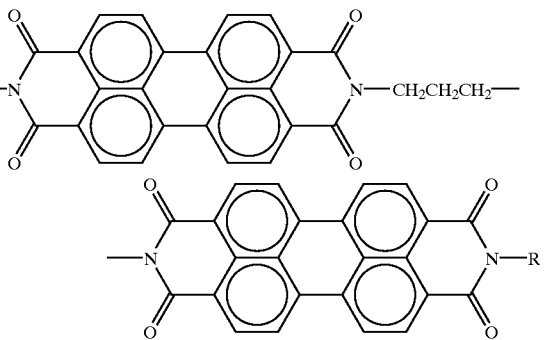

FORMULA 1 wherein R is hydrogen, alkyl, cycloalkyl, substituted alkyl, aryl, substituted aryl, aralkyl or substituted aralkyl, and at least one terminally unsymmetrical dimer of Formula 2

FORMULA 2 wherein $R_1$ and $R_2$ are hydrogen, alkyl, cycloalkyl, substituted alkyl, aryl, substituted aryl, aralkyl, or substituted aralkyl, and wherein $R_1$ and $R_2$ are dissimilar, which process comprises the condensation of a mixture of at least two perylene monoimide-monoanhydrides of Formula 3 with a diamine

FORMULA 3

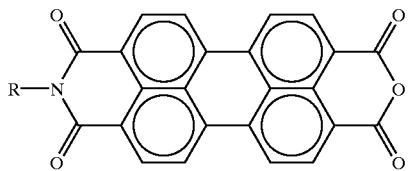

wherein R is hydrogen, alkyl, cycloalkyl, substituted alkyl, aryl, substituted aryl, aralkyl, and substituted aralkyl.

2. A process in accordance with claim 1 wherein the mixture of monoimide-monoanhydrides is comprised of a mixture of n-pentylmonoimide (Formula 3, R is n-pentyl) and 2-methylbutylmonoimide (Formula 3, R is 2-methylbutyl).

3. A process in accordance with claim 2 wherein the molar ratio, respectively, of n-pentylmonoimide and 2-methylbutylmonoimide is about 7:3.

4. A process in accordance with claim 2 wherein the molar ratio, respectively, of n-pentylmonoimide and 2-methylbutylmonoimide is about 6:4.

5. A process in accordance with claim 2 wherein the molar ratio, respectively, of n-pentylmonoimide and 2-methylbutylmonoimide is about 1:1.

6. A process in accordance with claim 2 wherein the molar ratio, respectively, of n-pentylmonoimide and 2-methylbutylmonoimide is about 4:6; is about 3:7; or is about 7:3.

7. A process in accordance with claim 1 wherein the mixture of monoimide-monoanhydrides is comprised of a mixture of n-butylmonoimide (Formula 3, R is n-butyl), n-pentylmonoimide (Formula 3, R is n-pentyl) and 2-methylbutylmonoimide (Formula 3, R is 2-methylbutyl).

8. A process in accordance with claim 7 wherein the mixture of monoimide-monoanhydrides is comprised of an equimolar mixture of n-butylmonoimide (Formula 3, R is n-butyl), n-pentylmonoimide (Formula 3, R is n-pentyl) and 2-methylbutylmonoimide (Formula 3, R is 2-methylbutyl).

9. A process in accordance with claim 1 wherein said condensation is accomplished by heating in the presence of a solvent.

10. A composition comprised of a mixture of at least two symmetrical perylene bisimide dimers of Formula 1

FORMULA 1

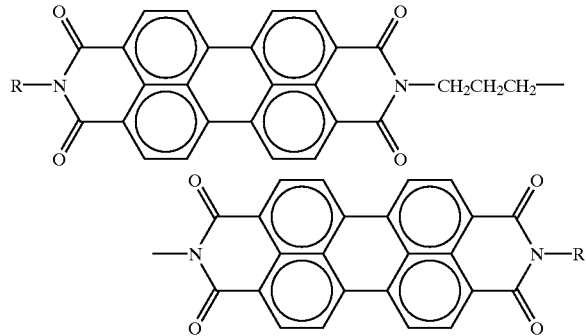

wherein R is hydrogen, alkyl, cycloalkyl, substituted alkyl, aryl, substituted aryl, aralkyl or substituted aralkyl, and at least one terminally unsymmetrical dimer of Formula 2

FORMULA 2

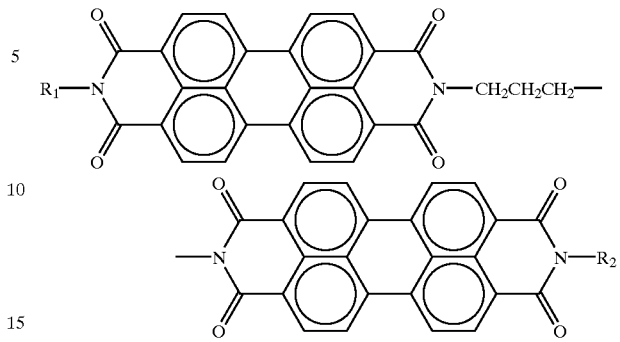

wherein $R_1$ and $R_2$ are hydrogen, alkyl, cycloalkyl, substituted alkyl, aryl, substituted aryl, aralkyl, or substituted aralkyl, and wherein $R_1$ and $R_2$ are dissimilar.

11. A composition in accordance with claim 10 wherein the mixture is comprised of the three dimers corresponding to Formula 1 wherein R is n-pentyl, Formula 1 wherein R is 2-methylbutyl, and Formula 2 wherein $R_1$ is n-pentyl and $R_2$ is 2-methylbutyl.

12. A composition in accordance with claim 11 wherein the mixture is comprised of about 25 percent of Formula 1 wherein R is n-pentyl, 25 percent of Formula 1 wherein R is 2-methylbutyl, and 50 percent of Formula 2 wherein $R_1$ is n-pentyl and $R_2$ is 2-methylbutyl.

13. A composition in accordance with claim 10 wherein the mixture is comprised of about 36 percent of Formula 1 wherein R is n-pentyl, 16 percent of Formula 1 wherein R is 2-methylbutyl, and 48 percent of Formula 2 wherein $R_1$ is n-pentyl and $R_2$ is 2-methylbutyl.

14. A composition in accordance with claim 10 wherein the mixture is comprised of the three dimers corresponding to Formula 1 wherein R is n-butyl, Formula 1 wherein R is n-hexyl, and Formula 2 wherein $R_1$ is n-butyl and $R_2$ is n-hexyl.

15. A composition in accordance with claim 10 wherein the mixture is comprised of about 25 percent of Formula 1 wherein R is n-butyl, 25 percent of Formula 1 wherein R is n-hexyl, and 50 percent of Formula 2 wherein $R_1$ is n-butyl and $R_2$ is n-hexyl.

16. A composition in accordance with claim 10 wherein the mixture is comprised of six dimers corresponding or encompassed by Formula 1 wherein R is n-butyl, Formula 1 wherein R is n-pentyl, Formula 1 wherein R is 2-methylbutyl, Formula 2 wherein $R_1$ is n-butyl and $R_2$ is n-pentyl, Formula 2 wherein $R_1$ is n-butyl and $R_2$ is 2-methylbutyl, and Formula 2 wherein $R_1$ is n-pentyl and $R_2$ is 2-methylbutyl.

17. A composition in accordance with claim 10 wherein the mixture is comprised, approximately, of a 1:1:1:2:2:2 ratio, respectively, of the six dimers of Formula 1 wherein R is n-butyl, Formula 1 wherein R is n-pentyl, Formula 1 wherein R is 2-methylbutyl, Formula 2 wherein $R_1$ is n-butyl and $R_2$ is n-pentyl, Formula 2 wherein $R_1$ is n-butyl and $R_2$ is 2-methylbutyl, and Formula 2 wherein $R_1$ is n-pentyl and $R_2$ is 2-methylbutyl.

18. A composition in accordance with claim 10 wherein substituted aralkyl is 2-, 3-, or 4-hydroxybenzyl, 2-, 3-, or 4-methylbenzyl, 2-, 3-, or 4-tertiary-butylbenzyl, 2-, 3-, or 4-methoxybenzyl, 2-, 3-, or 4-halobenzyl, 2-, 3-, or 4-nitrobenzyl, 2-, 3-, or 4-cyanophenyl, 2-, 3-, or 4-dimethylaminobenzyl, 2-, 3-, or 4-hydroxyphenethyl, 2-, 3-, or 4-methylphenethyl, 2-, 3-, or 4-tertiarybutylphenethyl, 2-, 3-, or 4-methoxyphenethyl, 2-, 3-, or 4-halophenethyl, 2-, 3-, or 4-nitrophenethyl, 2-, 3-, or 4-cyanophenethyl or 2-, 3-, or 4-dimethylaminophenethyl, and wherein halo is chloro, fluoro, iodo, or bromo.

19. A composition in accordance with claim 10 comprised of from about 2 to about 4 dimers of Formula 1, and from about 1 to about 5 dimers of Formula 2.

20. A composition in accordance with claim 10 comprised of from about 2 to about 3 dimers of Formula 1, and from about 1 to about 2 dimers of Formula 2.

21. A composition in accordance with claim 10 comprised of from about 3 to about 5 dimers of Formula 1, and about 1 to about 4 dimers of Formula 2.

22. A composition in accordance with claim 10 wherein said perylenes of Formulas 1 and 2 function as a photogenerating layer.

23. A composition in accordance with claim 10 wherein said alkyl contains from 1 to about 25 carbon atoms, and said aryl contains from 6 to about 36 carbon atoms.

24. A composition in accordance with claim 10 wherein aralkyl is benzyl, phenethyl or 3-phenylpropyl.

25. A composition in accordance with claim 10 wherein substituted aralkyl is 2-, 3-, or 4-hydroxybenzyl, 2-, 3-, or 4-methylbenzyl, 2-, 3-, or 4-tertiary-butylbenzyl, 2-, 3-, or 4-methoxybenzyl, 2-, 3-, or 4-halobenzyl, 2-, 3-, or 4-nitrobenzyl, 2-, 3-, or 4-cyanophenyl, 2-, 3-, or 4-dimethylaminobenzyl, 2-, 3-, or 4-hydroxyphenethyl, 2-, 3-, or 4-methylphenethyl, 2-, 3-, or 4-tertiary-butylphenethyl, 2-, 3-, or 4-methoxyphenethyl, 2-, 3-, 4-halophenethyl, 2-, 3-, or 4-nitrophenethyl, 2-, 3-, or 4-cyanophenethyl or 2-, 3-, or 4-dimethylaminophenethyl, and wherein halo is chloro, fluoro, iodo, or bromo.

26. A composition in accordance with claim 10 wherein $R_1$ and $R_2$ are methyl, ethyl, n-propyl, 3-methoxypropyl, n-butyl, isobutyl, n-pentyl, 2-pentyl, 3-pentyl, 2-methylbutyl, 3-methylbutyl, neopentyl, n-hexyl, n-heptyl, n-octyl, benzyl, 3-chlorobenzyl or phenethyl.

27. A composition in accordance with claim 10 wherein the mixture is comprised of three perylene dimers of Formula 1 wherein R is hydrogen, alkyl, cycloalkyl, or aryl, and a dimer of Formula 2 wherein $R_1$ is n-pentyl and $R_2$ is hydrogen.

28. A composition in accordance with claim 10 wherein the mixture is comprised of three dimers corresponding to Formula 1 wherein R is selected from hydrogen, alkyl, cycloalkyl, substituted alkyl, aryl, substituted aryl, aralkyl or substituted aralkyl, and Formula 2 wherein $R_1$ is n-butyl and $R_2$ is selected from hydrogen, alkyl, cycloalkyl, substituted alkyl, aryl, or substituted aryl.

29. A composition in accordance with claim 10 wherein the mixture is comprised of three dimers corresponding to Formula 1 wherein R is selected from hydrogen, alkyl, cycloalkyl, substituted alkyl, aryl, substituted aryl, aralkyl or substituted aralkyl, and Formula 2 wherein $R_1$ is n-hexyl and $R_2$ is selected from hydrogen, alkyl, cycloalkyl, substituted alkyl, aryl, or substituted aryl and wherein $R_2$ is identical to the R of Formula 1; or wherein the mixture is comprised of three dimers corresponding to Formula 1 wherein R is 3-chlorobenzyl, Formula 1 wherein R is selected from hydrogen, alkyl, cycloalkyl, substituted alkyl, aryl, substituted aryl, aralkyl or substituted aralkyl, and Formula 2 wherein $R_1$ is 3-chlorobenzyl and $R_2$ is selected from hydrogen, alkyl, cycloalkyl, substituted alkyl, aryl, or substituted aryl.

30. A composition in accordance with claim 10 wherein the mixture is comprised of three dimers corresponding to Formula 1 wherein R is selected from hydrogen, alkyl, cycloalkyl, substituted alkyl, aryl, substituted aryl, aralkyl or substituted aralkyl, and Formula 2 wherein $R_1$ is 2,3-dimethylpropyl and $R_2$ is selected from hydrogen, alkyl, cycloalkyl, substituted alkyl, aryl, or substituted aryl.

31. A composition in accordance with claim 10 wherein said composition is dispersed in a mixture of polyvinylbutyral (PVB) and polyvinyl carbazole (PVK).

32. A composition in accordance with claim 31 wherein said PVK is present in an amount of from about 0.5 to about 5 weight percent, and the total of said PVB and PVK is 100 percent.

33. A process in accordance with claim 1 wherein the diamine is 1,3-diaminopropane.

34. A process in accordance with claim 3 wherein the diamine is 1,3-diaminopropane.

35. A process in accordance with claim 7 wherein the diamine is 1,3-diaminopropane.

* * * * *